(12) United States Patent
Whittle

(10) Patent No.: US 10,179,683 B2
(45) Date of Patent: Jan. 15, 2019

(54) PHARMACEUTICAL FORMULATION

(71) Applicant: GW Pharma Limited, Salisbury (GB)

(72) Inventor: Brian Anthony Whittle, Hornsea (GB)

(73) Assignee: GW Pharma Limited, Cambridge (GB)

( * ) Notice: Subject to any disclaimer, the term of this patent is extended or adjusted under 35 U.S.C. 154(b) by 0 days.

(21) Appl. No.: 14/685,707

(22) Filed: Apr. 14, 2015

(65) Prior Publication Data

US 2016/0068321 A1    Mar. 10, 2016

Related U.S. Application Data

(63) Continuation of application No. 14/074,067, filed on Nov. 7, 2013, now Pat. No. 9,029,423, which is a continuation of application No. 13/486,227, filed on Jun. 1, 2012, now Pat. No. 8,603,515, which is a continuation of application No. 12/704,729, filed on Feb. 12, 2010, now Pat. No. 8,211,946, which is a continuation of application No. 11/229,052, filed on Sep. 16, 2005, now Pat. No. 7,709,536, which is a continuation of application No. 10/218,989, filed on Aug. 14, 2002, now Pat. No. 6,946,150.

(51) Int. Cl.
| | | |
|---|---|---|
| *A61K 31/05* | (2006.01) | |
| *B65D 65/38* | (2006.01) | |
| *A61K 9/00* | (2006.01) | |
| *A61K 31/352* | (2006.01) | |
| *A61K 36/185* | (2006.01) | |
| *B65B 31/00* | (2006.01) | |

(52) U.S. Cl.
CPC .............. *B65D 65/38* (2013.01); *A61K 9/006* (2013.01); *A61K 31/05* (2013.01); *A61K 31/352* (2013.01); *A61K 36/185* (2013.01); *B65B 31/00* (2013.01)

(58) Field of Classification Search
None
See application file for complete search history.

(56) References Cited

U.S. PATENT DOCUMENTS

| | | | |
|---|---|---|---|
| 6,503,532 B1 | 1/2003 | Murty et al. | |
| 6,713,048 B2 | 3/2004 | Peart et al. | |
| 6,730,330 B2 | 5/2004 | Whittle et al. | |
| 6,946,150 B2 | 9/2005 | Whittle | |
| 7,025,992 B2 | 4/2006 | Whittle et al. | |
| 7,622,140 B2* | 11/2009 | Whittle | B01D 11/0242 424/725 |
| 7,709,536 B2 | 5/2010 | Whittle | |
| 8,211,946 B2 | 7/2012 | Whittle | |
| 8,574,188 B2* | 11/2013 | Potter | A61M 5/30 604/57 |
| 8,603,515 B2 | 12/2013 | Whittle | |
| 9,029,423 B2 | 5/2015 | Whittle | |
| 9,034,395 B2* | 5/2015 | Whittle | B01D 11/0242 424/494 |
| 2002/0136752 A1 | 9/2002 | Whittle et al. | |
| 2004/0192760 A1* | 9/2004 | Whittle | A61K 9/0031 514/454 |

FOREIGN PATENT DOCUMENTS

| | | |
|---|---|---|
| GB | 2361869 A | 11/2001 |
| WO | WO 02/032420 A1 | 4/2002 |

OTHER PUBLICATIONS

Karhunen et al.(Piffalls in the Diagnosis of Drug Smuggler's Abdomen, Journal of Forensic Sciences, 1991, vol. 36, No. 2, pp. 397-402).*
U.S. Appl. No. 10/468,041, filed Apr. 22, 2004, Published, 2004-01927601.
U.S. Appl. No. 10/218,989, filed Aug. 14, 2002, Granted, U.S. Pat. No. 6,946,150.
U.S. Appl. No. 11/229,052, filed Sep. 16, 2005, Granted, U.S. Pat. No. 7,709,536.
U.S. Appl. No. 12/704,729, filed Feb. 12, 2010, Granted, U.S. Pat. No. 8,211,946.
U.S. Appl. No. 13/486,227, filed Jun. 1, 2012, Granted, U.S. Pat. No. 8,603,515.
U.S. Appl. No. 14/074,067, filed Nov. 7, 2013, Granted, U.S. Pat. No. 9,029,423.
The United Kingdom Parliament, Select Committee on Science and Technology Ninth Report (1998) at http://www.parliament.thestationery-office.co.uk/pa/ld199798/ldselect/ldsctech/151/15101.htm.
The United Kingdom Parliament, Select Committee on Science and Technology Second Report (Mar. 14, 2001) at http://www.publications.parliament.uk/pa/ld200001/ldselect/ldsctech/50/5001.htm.

* cited by examiner

*Primary Examiner* — Alton N Pryor
(74) *Attorney, Agent, or Firm* — Wolf, Greenfield & Sacks, P.C.

(57) ABSTRACT

The invention relates to pharmaceutical formulations, and more particularly to formulations containing cannabinoids for administration via a pump action spray. In particular, the invention relates to pharmaceutical formulations, for use in administration of lipophilic medicaments via mucosal surfaces, comprising: at least one lipophilic medicament, a solvent and a co-solvent, wherein the total amount of solvent and co-solvent present in the formulation is greater than 55% wt/wt of the formulation and the formulation is absent of a self emulsifying agent and/or a fluorinated propellant.

16 Claims, 11 Drawing Sheets

Fig. 2
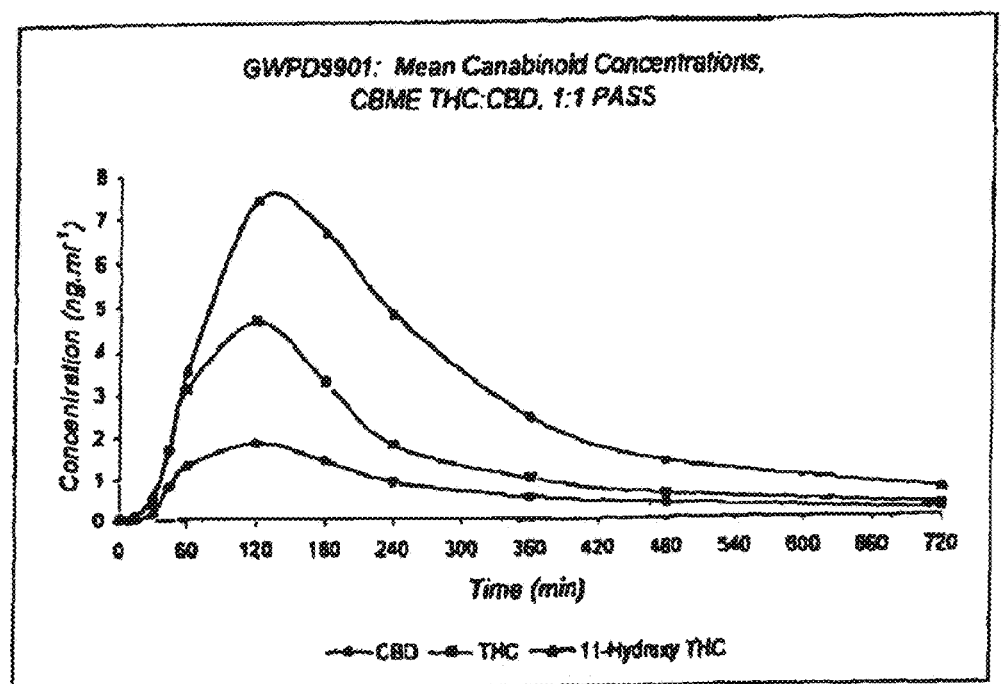
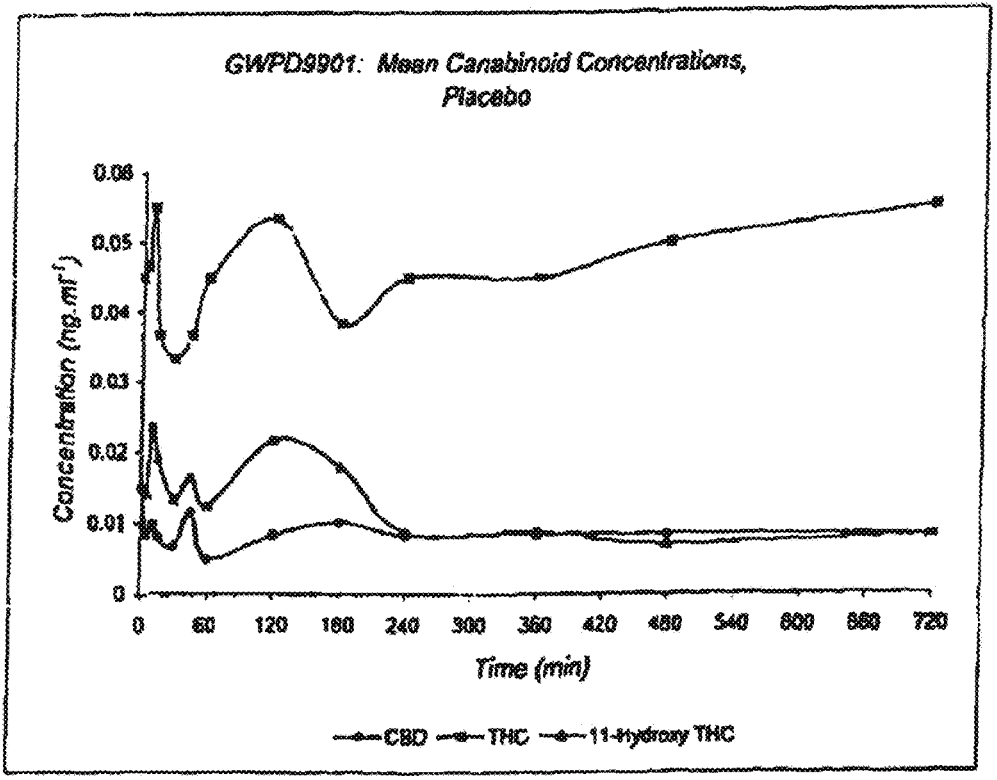

Fig. 5

AEROSOL PLUME CROSS SECTIONAL AREA VS VISCOSITY FOR PG/ETHANOL MIXTURES

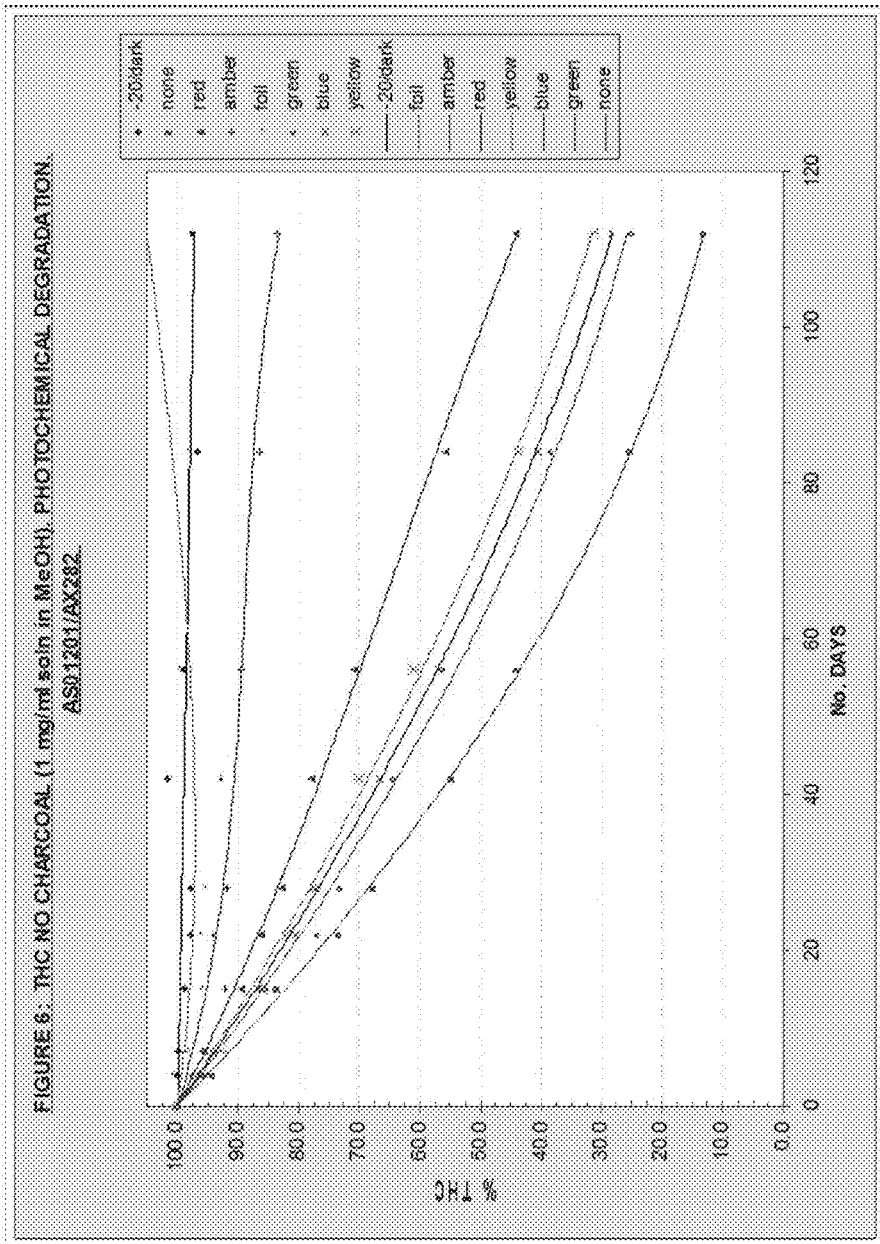

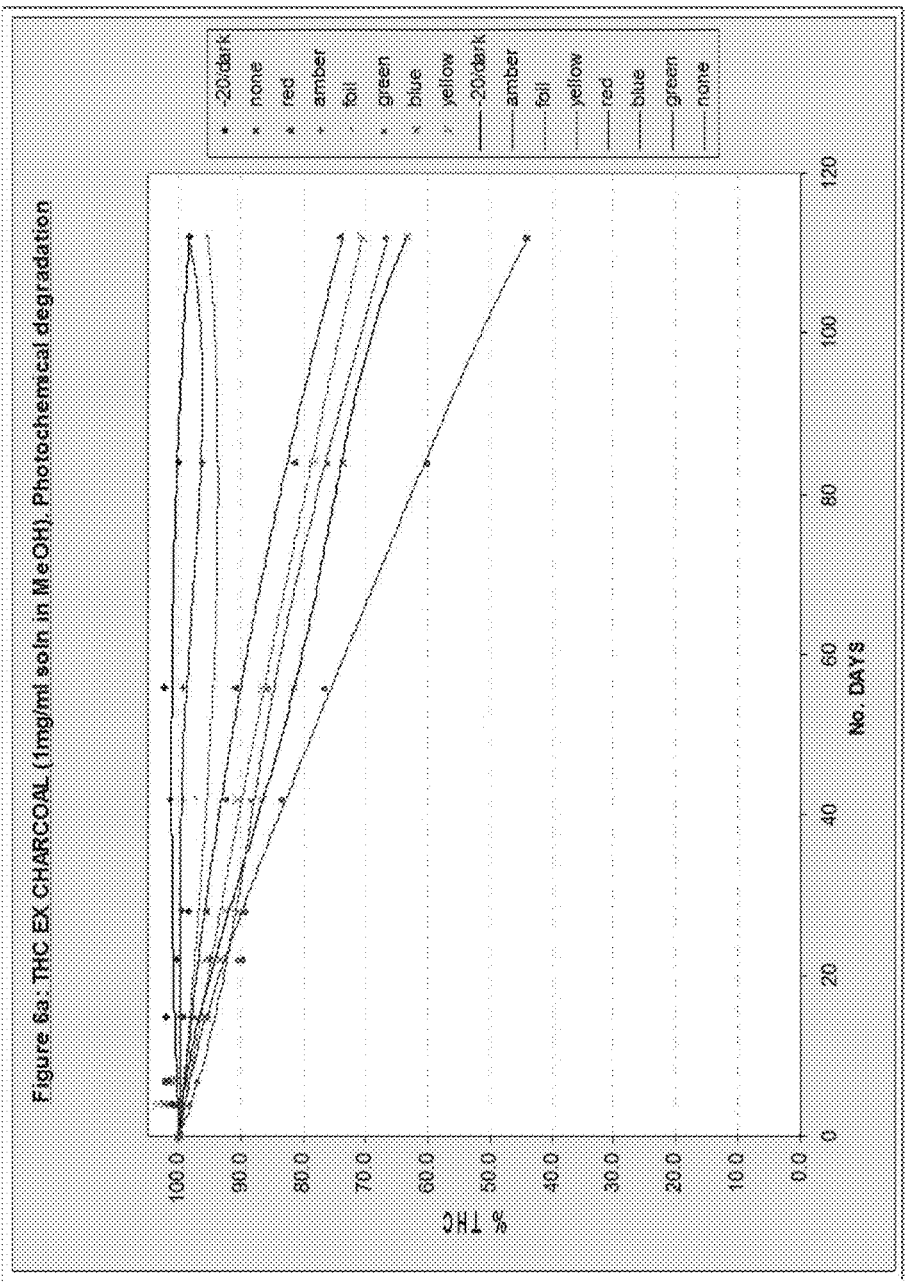

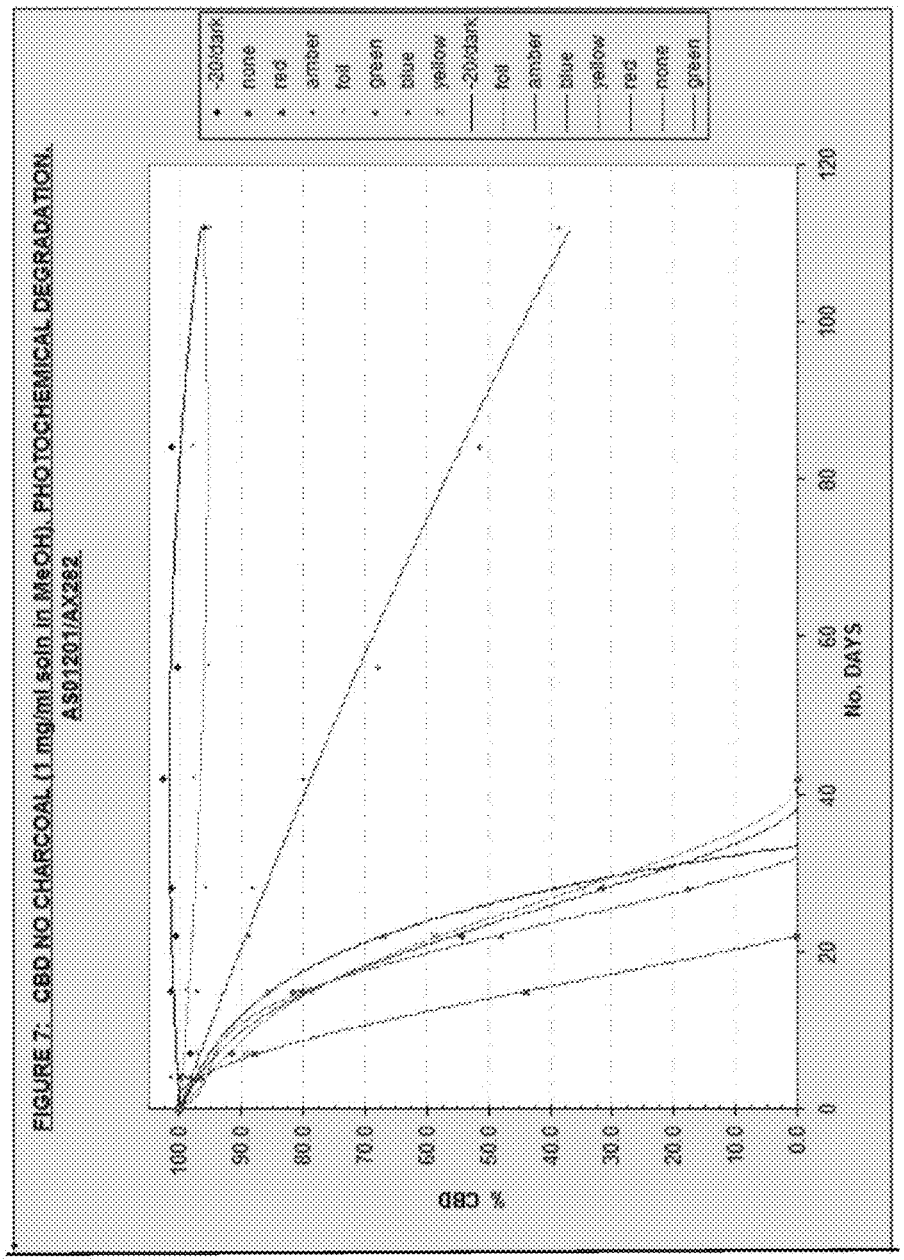

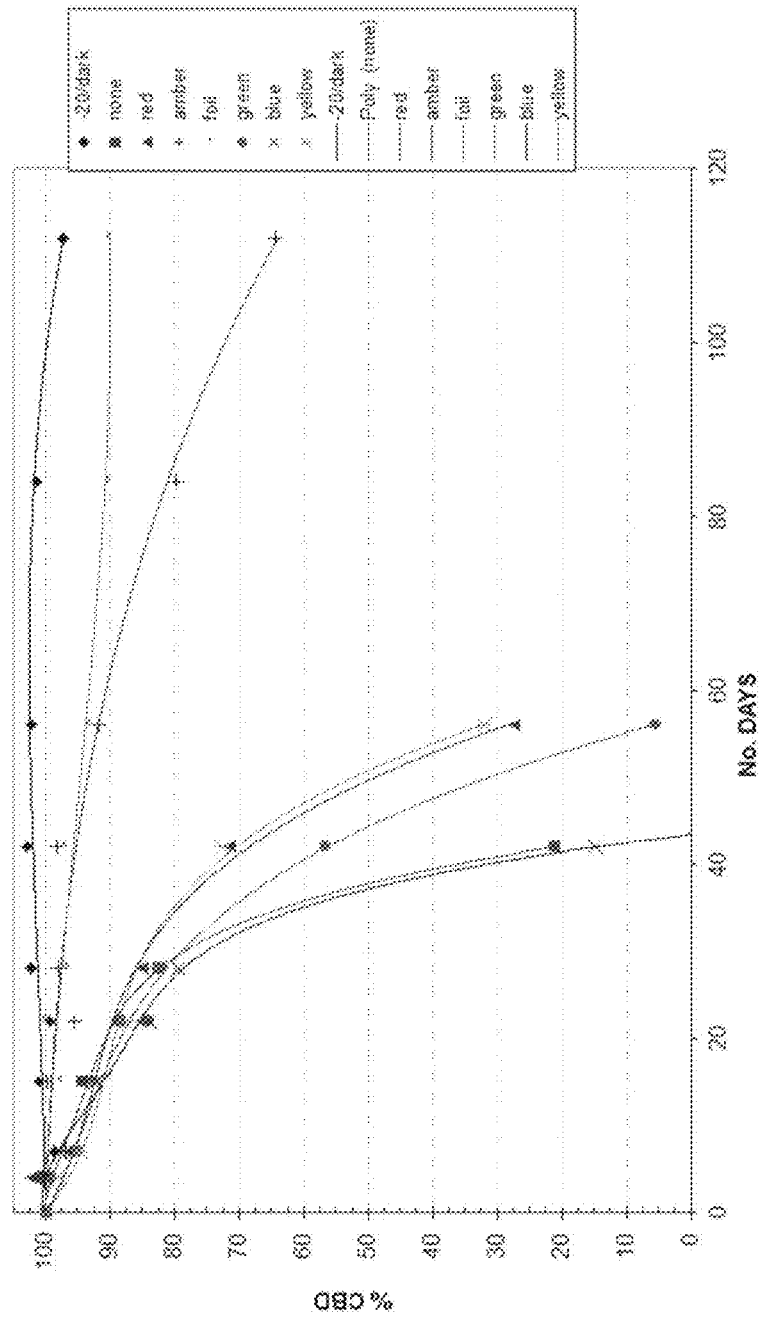

PHARMACEUTICAL FORMULATION

RELATED APPLICATIONS

This application is a continuation of U.S. patent application Ser. No. 14/074,067, filed Nov. 7, 2013, now U.S. Pat. No. 9,029,423, which is a continuation of U.S. patent application Ser. No. 13/486,227, filed Jun. 1, 2012, now U.S. Pat. No. 8,603,515, which is a continuation of U.S. patent application Ser. No. 12/704,729, filed Feb. 12, 2010, now U.S. Pat. No. 8,211,946, which is a continuation of U.S. patent application Ser. No. 11/229,052, filed Sep. 16, 2005, now U.S. Pat. No. 7,709,536, which is a continuation of U.S. patent application Ser. No. 10/218,989, filed Aug. 14, 2002, now U.S. Pat. No. 6,946,150, the entire contents of each of which are incorporated by reference herein.

FIELD OF THE INVENTION

The present invention relates to pharmaceutical formulations, and more particularly to formulations containing cannabinoids for administration via a pump action spray.

BACKGROUND OF THE INVENTION

It has long been known to introduce drugs into the systemic circulation system via a contiguous mucous membrane to increase onset of activity, potency etc.

For example, U.S. Pat. No. 3,560,625 disclose aerosol formulations for introducing an alkoxybenzamide into the systemic circulatory system. Two different types of aerosol formulations are disclosed:
a) fluorinated hydrocarbon type comprising 2% by weight alkoxybenzamide, 18% ethanol, and 80% propellant; and
b) nebuliser type comprising 0.5% by weight alkoxybenzamide, a mixed solvent system comprising 10.3% ethanol and 31.4% propylene glycol and 57.8% deionised water.

U.S. Pat. No. 3,560,625 identifies a problem in finding a suitable solvent system to produce an aerosol spray for inhalation of the ortho-ethoxybenzamide, due to the fact that whilst ethanol was undoubtedly the best solvent, a mixture containing more than 18% of ethanol by weight produced an unpleasant oral reaction which more than counterbalanced the efficacy of the oral route.

When the present applicant set out to produce spray formulations for a botanical drug substance comprising one or more cannabinoids they were aware that the highly lipophylic nature of the cannabinoids could present problems in formulating the active component(s).

The present applicant first sought to develop a formulation for oromucosal, preferably sublingual, delivery in a pressurised aerosol or spray form, as disclosed in international patent application PCT/GB01/01027. Their initial focus was on propellant driven systems with HFC-123a and HFC-227 but these proved to be unsuitable as solvents for the cannabinoids. The formulations comprised synthetic Δ9-THC in amounts from 0.164 to 0.7% wt/wt, with ethanol as the primary solvent in amounts up to 20.51% by weight. One particular composition comprised 0.164% synthetic Δ9-THC, 4.992% ethanol, 4.992% propylene glycol and 89.582% p134a (propellant).

The applicant found that even at ethanol levels of 20% by volume of the total formulation volume they were unable to dissolve sufficient levels of Δ9-THC in a standard spray dose to meet clinical needs, because of the cannabinoids poor solubility in the propellant. They also found that the ethanol level could not be increased, as the delivery characteristics of the device nozzle altered substantially when the lower volatility solvents were increased above a critical ratio. The HFC-123a and HFC-227 propellant sprays delivered a maximum of 7 mg/ml, whereas initial clinical studies suggested the formulations would be required to contain up to 50 mg cannabinoids/ml.

Thus, the present applicants focussed on self-emulsifying drug delivery systems, as are discussed in detail in a review article European Journal of Pharmaceutics and Biopharmaceutics 50 (2000) 179-188, which concluded that the poor aqueous solubility of many chemical entities represents a real challenge for the design of appropriate formulations aimed at enhancing oral bioavailability.

In their co-pending International application PCT/GB02/00620 the applicant discloses a wide range of cannabinoid-containing formulations containing at least one self-emulsifying agent. The inclusion of at least one self-emulsifying agent was thought necessary to get the formulation to adhere to the mucosal surface in order to achieve sufficient absorption of the cannabinoids. One particular formulation comprised 2% by wt glycerol mono-oleate, 5% CBME of G1 cannabis to give THC, 5% CBME of G5 cannabis to give CBD, 44% ethanol BP and 44% propylene glycol.

SUMMARY OF THE INVENTION

Surprisingly, the applicant has found that they do not absolutely require the presence of a self-emulsifying agent in a liquid formulation to achieve a satisfactory dosage level by oromucosal, and specifically sub-lingual or buccal, application.

Indeed, contrary to the teachings of U.S. Pat. No. 3,560,625 and the European Journal of Pharmaceutics and Biopharmaceutics 50 (2000) 179-188, they have been able to produce a simple and effective vehicle for delivering a lipophilic medicament in a liquid spray.

According to a specific aspect of the present invention there is provided a pharmaceutical formulation consisting essentially of one or more cannabinoids, ethanol and propylene glycol.

Preferably the one or more cannabinoids are present in the form of at least one extract from at least one *cannabis* plant. The *cannabis* plant(s) preferably include at least one *cannabis* chemovar. Most preferably the plant extract will be a botanical drug substance (BDS), as defined herein.

Optionally, the formulation may additionally contain a flavour, such as, for example, peppermint oil.

The formulation may also contain, in addition to the cannabinoid(s), a further active agent, which is preferably an opiate, for example morphine. Thus, it is contemplated to provide a formulation consisting essentially of one or more cannabinoids, ethanol, propylene glycol and an opiate, preferably morphine.

A typical liquid pharmaceutical formulation according to this specific aspect of the invention, given by way of example and not intended to be limiting to the invention, may contain in a 1 ml vol: THC 25-50 mg/ml, preferably 25 mg/ml (based on amount of cannabinoid in a botanical drug substance), CBD 25-50 mg/ml, preferably 25 mg/ml (based on amount of cannabinoid in a botanical drug substance), propylene glycol 0.5 ml/ml, peppermint oil 0.0005 ml/ml, and ethanol (anhydrous) qs to 1 ml.

Other preferred formulations include a "high THC" formulation comprising in a 1 ml vol: THC 25 mg/ml (based on amount of cannabinoid in a botanical drug substance), propylene glycol 0.5 peppermint oil 0.0005 ml/ml, and ethanol (anhydrous) qs to 1 ml; and a "high CBD" formulation comprising in a 1 ml vol: CBD 25 mg/ml (based on amount of cannabinoid in a botanical drug substance), propylene glycol 0.5 ml/ml, peppermint oil 0.0005 ml/ml, and ethanol (anhydrous) qs to 1 ml.

In these formulations the cannabinoids are added as botanical drug substances derived from *cannabis* plants, quoted amounts of cannabinoids correspond to total amount (weight) of cannabinoid present in 1 ml of the final formulation. The skilled reader will appreciate that the total amount of BDS which must be added in order to achieve the desired amount of cannabinoid in the final formulation will be dependent on the concentration of cannabinoid present in the BDS, which will vary between different batches of BDS.

The finding that such a simple combination of one or more cannabinoids, ethanol and propylene glycol can be used effectively in a pump action spray was unexpected.

The applicant has found that, where the solvent/co-solvent system is ethanol/propylene glycol and the lipophilic medicament comprises one or more cannabinoids in the form of a botanical drug substance (BDS), the limits in which the solvent/co-solvent will work effectively are quite narrow, as discussed below.

More broadly speaking, and according to a general aspect of the invention, there is provided a liquid pharmaceutical formulation, for use in administration of a lipophilic medicament via a mucosal surface, comprising at least one lipophilic medicament, a solvent and a co-solvent, wherein the total amount of solvent and co-solvent present in the formulation is greater than 55% wt/wt of the formulation and the formulation is absent of a self-emulsifying agent and/or a fluorinated propellant.

Preferably the amount of solvent/co-solvent is greater than 80%, more preferably in the order 90-98%.

Preferably the formulation has a water content of less than 5%.

Preferably the formulation does not contain any type of propellant.

The formulation also lacks any self-emulsifying agent. Self-emulsifying agents are defined herein as an agent which will form an emulsion when presented with an alternate phase with a minimum energy requirement. In contrast, an emulsifying agent, as opposed to a self-emulsifying agent, is one requiring additional energy to form an emulsion. Generally a self-emulsifying agent will be a soluble soap, a salt or a sulphated alcohol, especially a non-ionic surfactant or a quaternary compound. Exemplary self-emulsifying agents include, but are not limited to, glyceryl mono oleate (esp. SE grade), glyceryl monostearate (esp. SE grade), macrogols (polyethylene glycols), and polyoxyhydrogenated castor oils e.g. cremophor.

The formulation may additionally comprise a flavouring. The preferred flavouring is peppermint oil, preferably in an amount by volume of up to 0.1%, typically 0.05% v/v.

Preferably the solvent is selected from C1-C4 alcohols. The preferred solvent is ethanol.

Preferably the co-solvent is a solvent which allows a lower amount of the "primary" solvent to be used. In combination with the "primary" solvent it should solubilise the lipophylic medicament sufficiently that a medically useful amount of the lipophylic medicament is solubilised. A medically useful amount will vary with the medicament, but for cannabinoids will be an amount of at least 1.0 mg/0.1 ml of solvent/co-solvent.

Preferred co-solvents are selected from glycols, sugar alcohols, carbonate esters and chlorinated hydrocarbons.

The glycols are preferably selected from propylene glycol and glycerol, with propylene glycol being most preferred. The carbonate ester is preferably propylene carbonate.

The most preferred combination is ethanol as the solvent and propylene glycol as the co-solvent.

The preparation of liquid formulations for oropharangeal delivery of cannabinoids poses a number of problems. First, it is necessary to deliver at least 1.0 mg, more preferably at least 2.5 mg and even more preferably at least 5 mg of cannabinoids per 0.1 ml of liquid formulation to achieve a therapeutic effect in a unit dose. In this regard a patient may require up to 120 mg cannabinoid/day, on average around 40 mg/day to be taken in a maximum of six doses.

In the case of a sublingual or buccal delivery, this means delivering this quantity of the active ingredient in an amount of formulation which will not be swallowed by the patient, if the active ingredient is to be absorbed transmucosally.

Whilst such amounts can be achieved by dissolving the cannabinoid in ethanol as the solvent, high concentrations of ethanol provoke a stinging sensation and are beyond the limit of tolerability.

There is thus a need to use a co-solvent in order to reduce the amount of ethanol, whilst still enabling sufficient quantities of cannabinoid to be solubilised.

The applicant has discovered that the choice of co-solvent is limited. Preferred co-solvents should have a solubilizing effect sufficient to allow enough cannabinoid to be solubilised in a unit dose, namely at least 1.0 mg/0.1 ml of formulation, and which allows the amount of solvent present to be reduced to a level which is within the limits of patient tolerability. Particularly suitable co-solvents which fulfil these criteria are propylene glycol and glycerol.

In a preferred embodiment the total amount of solvent and co-solvent present in the formulation, is greater than about 65% w/w, more preferably greater than about 70% w/w, more preferably greater than about 75% w/w, more preferably greater than about 80% w/w, more preferably greater than about 85% w/w of the formulation. Most preferably the total amount of solvent and co-solvent present in the formulation is in the range from about 80% w/w to about 98% w/w of the formulation.

In a preferred embodiment the formulations according to the invention are liquid formulation administered via a pump-action spray. Pump-action sprays are characterised in requiring the application of external pressure for actuation, for example external manual, mechanical or electrically initiated pressure. This is in contrast to pressurized systems, e.g. propellant-driven aerosol sprays, where actuation is typically achieved by controlled release of pressure e.g. by controlled opening of a valve.

Pump-action sprays are found to be particularly beneficial when it comes to delivering cannabinoids. Indeed, previously people have focussed their attention on solvent systems including a propellant.

Whilst it has been recognised that there are disadvantages with such systems, including the speed of delivery, those skilled in the art have tried to address this by slowing the propellant or by altering the nozzle. The applicants have found that by using a pump spray with their formulations they are able to produce a spray in which the particles have a mean aerodynamic particle size of between 15 and 45 microns, more particularly between 20 and 40 microns and an average of about 33 microns. These contrast with particles having a mean aerodynamic particle size of between 5 and 10 microns when delivered using a pressurised system.

In fact, comparative tests by the applicant have shown such a pump-action spray system to have advantages in being able to deliver the active components to a larger surface area within the target area. This is illustrated with reference to the accompanying Example 3.

The variation in particle distribution and sprayed area has been demonstrated by direct experiment. A formulation as described in the accompanying Example 4 was filled into a pump action spray assembly (Valois vial type VP7100 actuated). The same formulation was filled into a pressurised container powered by HFA 134a.

Both containers were discharged at a distance of 50 mm from a sheet of thin paper held at right angles to the direction of travel of the jet. The pattern of spray produced in both cases by discharge of 100 µl was then visualised against the light. In both cases the pattern of discharge was circular and measurements were as follows:

|  | Mean Diameter (mm) | Mean Area (mm$^2$) |
| --- | --- | --- |
| Pump Action Spray | 23 | 425.5 |
| Pressurised Spray | 16 | 201.1 |

The pressurised spray produced pooling of liquid at the centre of the area. The pump action spray gave a more even spray pattern and less "bounce back". There was also a significantly greater area covered by the pump action spray. The conditions under which this test was carried out are relevant to the in-practice use of the device. A wider area of buccal mucosa can be reached by the pump action spray compared with the pressurised spray.

For pump spray applications the solvent/co-solvent combination must have a viscosity within the viscosity range defined by the preferred solvent/co-solvent combination. Thus it should be a viscosity ranging between that for an ethanol/propylene glycol combination where the ethanol/propylene glycol are present in the relative proportions by volume of 60/40 and 40/60, more preferably still 55/45 to 45/55 and most preferably about 50/50.

The viscosity of the resulting formulation when packaged for delivery by pump action through a mechanical pump such as, for example, a VP7 actuator valve (Valois), allows the resulting aerosol to deliver a spray having a mean aerodynamic particle size of from 20-40 microns, more preferably 25-35 and most preferably with an average particle size of from 30-35 microns. This maximises contact with the target mucosal membrane for sublingual/buccal delivery.

Preferably the formulations according to the general and specific aspects of the invention comprises as the lipophilic medicament one or more cannabinoids.

Preferably the lipophilic medicament is at least one extract from at least one *cannabis* plant. The *cannabis* plant(s) preferably include at least one *cannabis* chemovar. Most preferably the plant extract will be a botanical drug substance (BDS), as defined herein.

A "plant extract" is an extract from a plant material as defined in the Guidance for Industry Botanical Drug Products Draft Guidance, August 2000, US Department of Health and Human Services, Food and Drug Administration Center for Drug Evaluation and Research.

"Plant material" is defined as a plant or plant part (e.g. bark, wood, leaves, stems, roots, flowers, fruits, seeds, berries or parts thereof) as well as exudates.

The term "*Cannabis* plant(s)" encompasses wild type *Cannabis sativa* and also variants thereof, including *cannabis* chemovars which naturally contain different amounts of the individual cannabinoids, *Cannabis sativa* subspecies *indica* including the variants var. *indica* and var. *kafiristanica, Cannabis indica* and also plants which are the result of genetic crosses, self-crosses or hybrids thereof. The term "*Cannabis* plant material" is to be interpreted accordingly as encompassing plant material derived from one or more *cannabis* plants. For the avoidance of doubt it is hereby stated that "*cannabis* plant material" includes dried *cannabis* biomass.

In the context of this application the terms "*cannabis* extract" or "extract from a *cannabis* plant", which are used interchangeably, encompass "Botanical Drug Substances" derived from *cannabis* plant material. A Botanical Drug Substance is defined in the Guidance for Industry Botanical Drug Products Draft Guidance, August 2000, US Department of Health and Human Services, Food and Drug Administration Center for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of *cannabis*, "botanical drug substances" derived from *cannabis* plants do not include highly purified, Pharmacopoeial grade cannabinoids.

"*Cannabis* based medicine extracts (CBMEs)", such as the CBMEs prepared using processes described in the accompanying examples, are classified as "botanical drug substances", according to the definition given in the Guidance for Industry Botanical Drug Products Draft Guidance, August 2000, US Department of Health and Human Services, Food and Drug Administration Center for Drug Evaluation and Research.

"Botanical drug substances" derived from *cannabis* plants include primary extracts prepared by such processes as, for example, maceration, percolation, extraction with solvents such as C1 to C5 alcohols (e.g. ethanol), Norflurane (HFA134a), HFA227 and liquid carbon dioxide under sub-critical or super-critical conditions. The primary extract may be further purified for example by super-critical or sub-critical solvent extraction, vaporisation or chromatography. When solvents such as those listed above are used, the resultant extract contains non-specific lipid-soluble material. This can be removed by a variety of processes including "winterisation", which involves chilling to −20° C. followed by filtration to remove waxy ballast, extraction with liquid carbon dioxide and by distillation.

In the case where the cannabinoids are provided as a BDS, the BDS is preferably obtained by $CO_2$ extraction, under sub-critical or super-critical conditions, followed by a secondary extraction, e.g. an ethanolic precipitation, to remove a substantial proportion of waxes and other ballast. This is because the ballast includes wax esters and glycerides, unsaturated fatty acid residues, terpenes, carotenes, and flavenoids which are not very soluble in the chosen solvent/co-solvent, particularly the preferred co-solvent, propylene glycol, and will precipitate out. Most preferably the BDS is produced by a process comprising decarboxylation, extraction with liquid carbon dioxide and then a further extraction to remove significant amounts of ballast. Most preferably the ballast is substantially removed by an ethanolic precipitation.

Most preferably, *cannabis* plant material is heated to a defined temperature for a defined period of time in order to decarboxylate cannabinoid acids to free cannabinoids prior to extraction of the BDS.

Preferred "botanical drug substances" include those which are obtainable by using any of the methods or processes specifically disclosed herein for preparing extracts from *cannabis* plant material. The extracts are preferably substantially free of waxes and other non-specific lipid soluble material but preferably contain substantially all of the cannabinoids naturally present in the plant, most preferably in substantially the same ratios in which they occur in the intact *cannabis* plant.

Botanical drug substances are formulated into "Botanical Drug Products" which are defined in the Guidance for Industry Botanical Drug Products Draft Guidance, August 2000, US Department of Health and Human Services, Food and Drug Administration Center for Drug Evaluation and Research as: "A botanical product that is intended for use as a drug; a drug product that is prepared from a botanical drug substance."

"*Cannabis* plants" includes wild type *Cannabis sativa* and variants thereof, including *cannabis* chemovars which naturally contain different amounts of the individual cannabinoids.

The term "cannabinoids" also encompasses highly purified, Pharmacopoeial Grade substances, which may be obtained by purification from a natural source or via synthetic means. Thus, the formulations according to the invention may be used for delivery of extracts of *cannabis* plants and also individual cannabinoids, or synthetic analogues thereof, whether or not derived from *cannabis* plants, and also combinations of cannabinoids.

Preferred cannabinoids include, but are not limited to, tetrahydrocannabinoids, their precursors, alkyl (particularly propyl) analogues, cannabidiols, their precursors, alkyl (particularly propyl) analogues, and cannabinol. In a preferred embodiment the formulations may comprise any cannabinoids selected from tetrahydrocannabinol, $\Delta^9$-tetrahydrocannabinol (THC), $\Delta^8$-tetrahydrocannabinol, $\Delta^9$-tetrahydrocannabinol propyl analogue (THCV), cannabidiol (CBD), cannabidiol propyl analogue (CBDV), cannabinol (CBN), cannabichromene, cannabichromene propyl analogue and cannabigerol, or any combination of two or more of these cannabinoids. THCV and CBDV (propyl analogues of THC and CBD, respectively) are known cannabinoids which are predominantly expressed in particular *Cannabis* plant varieties and it has been found that THCV has qualitative advantageous properties compared with THC and CBD respectively. Subjects taking THCV report that the mood enhancement produced by THCV is less disturbing than that produced by THC. It also produces a less severe hangover.

Most preferably the formulations will contain THC and/or CBD.

In a preferred embodiment the formulations may contain specific, pre-defined ratios by weight of different cannbinoids, e.g. specific ratios of CBD to THC, or tetrahydrocannabinovarin (THCV) to cannabidivarin (CBDV), or THCV to THC. Certain specific ratios of cannabinoids have been found to be clinically useful in the treatment or management of specific diseases or medical conditions. In particular, certain of such formulations have been found to be particularly useful in the field of pain relief and appetite stimulation.

It has particularly been observed by the present applicant that combinations of specific cannabinoids are more beneficial than any one of the individual cannabinoids alone. Preferred embodiments are those formulations in which the amount of CBD is in a greater amount by weight than the amount of THC. Such formulations are designated as "reverse-ratio" formulations and are novel and unusual since, in the various varieties of medicinal and recreational *Cannabis* plant available world-wide, CBD is the minor cannabinoid component compared to THC. In other embodiments THC and CBD or THCV and CBDV are present in approximately equal amounts or THC or THCV are the major component and may be up to 95.5% of the total cannabinoids present.

Preferred formulations contain THC and CBD in defined ratios by weight. The most preferred formulations contain THC and CBD in a ratio by weight in the range from 0.9:1.1 to 1.1:0.9 THC:CBD, even more preferably the THC:CBD ratio is substantially 1:1. Other preferred formulations contain the following ratios by weight of THC and CBD:— greater than or equal to 19:1 THC:CBD, greater than or equal to 19:1 CBD:THC, 4.5:1 THC:CBD, 1:4 THC:CBD and 1:2.7 THC:CBD. For formulations wherein the THC:CBD ratio is substantially 1:1 it is preferred that the formulation includes about 2.5 g/ml of each of THC and CBD.

*Cannabis* has been used medicinally for many years, and in Victorian times was a widely used component of prescription medicines. It was used as a hypnotic sedative for the treatment of "hysteria, delirium, epilepsy, nervous insomnia, migraine, pain and dysmenorrhoea". The use of *cannabis* continued until the middle of the twentieth century, and its usefulness as a prescription medicine is now being re-evaluated. The discovery of specific cannabinoid receptors and new methods of administration have made it possible to extend the use of *cannabis*-based medicines to historic and novel indications.

The recreational use of *cannabis* prompted legislation which resulted in the prohibition of its use. Historically, *cannabis* was regarded by many physicians as unique; having the ability to counteract pain resistant to opioid analgesics, in conditions such as spinal cord injury, and other forms of neuropathic pain including pain and spasm in multiple sclerosis.

In the United States and Caribbean, *cannabis* grown for recreational use has been selected so that it contains a high content of tetrahydrocannabinol (THC), at the expense of other cannabinoids. In the Merck Index (1996) other cannabinoids known to occur in *cannabis* such as cannabidiol and cannabinol were regarded as inactive substances. Although cannabidiol was formerly regarded as an inactive constituent there is emerging evidence that it has pharmacological activity, which is different from that of THC in several respects. The therapeutic effects of *cannabis* cannot be satisfactorily explained just in terms of one or the other "active" constituents.

It has been shown that tetrahydrocannabinol (THC) alone produces a lower degree of pain relief than the same quantity of THC given as an extract of *cannabis*. The pharmacological basis underlying this phenomenon has been investigated. In some cases, THC and cannabidiol (CBD) have pharmacological properties of opposite effect in the same preclinical tests, and the same effect in others. For example, in some clinical studies and from anecdotal reports there is a perception that CBD modifies the psychoactive effects of THC. This spectrum of activity of the two cannabinoids may help to explain some of the therapeutic benefits of *cannabis* grown in different regions of the world. It also points to useful effects arising from combinations of THC and CBD. These have been investigated by the applicant. Table 1 below shows the difference in pharmacological properties of the two cannabinoids.

TABLE 1

| Effect | THC | THCV | CBD | CBDV | Reference |
|---|---|---|---|---|---|
| CB$_1$ (Brain receptors) | ++ | | ± | | Pertwee et al, 1998 |
| CB$_2$ (Peripheral receptors) | + | | − | | |
| CNS Effects | | | | | |
| Anticonvulsant † | −− | | ++ | | Carlini et al, 1973 |
| Antimetrazol | − | | − | | GW Data |
| Anti-electroshock | − | | ++ | | GW data |
| Muscle Relaxant | −− | | ++ | | Petro, 1980 |
| Antinociceptive | ++ | | + | | GW data |
| Catalepsy | ++ | | ++ | | GW data |
| Psychoactive | ++ | | − | | GW data |
| Antipsychotic | − | | ++ | | Zuardi et al, 1991 |
| Neuroprotective antioxidant activity* | + ++ | | ++ − | | Hampson A J et al, 1998 |
| Antiemetic | + | | + | | |
| Sedation (reduced spontaneous activity) | ++ | | | | Zuardi et al, 1991 |
| Appetite stimulation | | | ++ | | |
| Appetite suppression | − | | ++ | | |
| Anxiolytic | | | | | GW data |
| Cardiovascular Effects | | | | | |
| Bradycardia | − | | + | | Smiley et al, 1976 |
| Tachycardia | + | | − | | |
| Hypertension § | + | | − | | |
| Hypotension § | − | | + | | Adams et al, 1977 |
| Anti-inflammatory Immunomoclulatory/ anti-inflammatory activity | ± | | ± | | Brown, 1998 |
| Raw Paw Oedema Test | − | | ++ | | GW data |
| Cox 1 | | | | | GW data |
| Cox 2 | | | | | GW data |
| TNFα Antagonism | + | + | ++ | ++ | |
| Glaucoma | ++ | | + | | |

*Effect is CB1 receptor independent.
† THC is pro convulsant
§ THC has a biphasic effect on blood pressure; in naïve patients it may produce postural hypotension and it has also been reported to produce hypertension on prolonged usage.

From these pharmacological characteristics and from direct experiments carried out by the applicant it has been shown, surprisingly, that combinations of THC and CBD in varying proportions are particularly useful in the treatment of certain therapeutic conditions. It has further been found clinically that the toxicity of a mixture of THC and CBD is less than that of THC alone.

Accordingly, the invention provides pharmaceutical formulations, having all the essential features described above, which comprise cannabinoids as the active agents and which have specific ratios of CBD to THC, which have been found to be clinically useful in the treatment or management of specific diseases or medical conditions.

In a further aspect the invention also relates to pharmaceutical formulations having all the essential features defined above, and which have specific ratios of tetrahydrocannabinovarin (THCV) or cannabidivarin (CBDV). THCV and CBDV (propyl analogues of THC and CBD, respectively) are known cannabinoids which are predominantly expressed in particular Cannabis plant varieties and it has been found that THCV has qualitative advantageous properties compared with THC and CBD respectively. Subjects taking THCV report that the mood enhancement produced by THCV is less disturbing than that produced by THC. It also produces a less severe hangover.

The invention still further relates to pharmaceutical formulations, having all the essential features as defined above, which have specific ratios of THCV to THC. Such formulations have been found to be particularly useful in the field of pain relief and appetite stimulation.

It has particularly been observed by the present applicants that the combinations of the specific cannabinoids are more beneficial than any one of the individual cannabinoids alone. Preferred embodiments are those formulations in which the amount of CBD is in a greater amount by weight than the amount of THC. Such formulations are designated as "reverse-ratio" formulations and are novel and unusual since, in the various varieties of medicinal and recreational Cannabis plant available world-wide, CBD is the minor cannabinoid component compared to THC. In other embodiments THC and CBD or THCV and CBDV are present in approximately equal amounts or THC or THCV are the major component and may be up to 95.5% of the total cannabinoids present.

Particularly preferred ratios of cannabinoids and the target medical conditions for which they are suitable are shown in Table 2 below. Other preferred ratios of THC:CBD, THCV:CBDV and THC:TCHV and preferred therapeutic uses of such formulations are set out in the accompanying claims.

TABLE 2

Target Therapeutic Groups for Different Ratios of Cannabinoid

| Product group | Ratio THC:CBD | Target Therapeutic Area |
|---|---|---|
| High THC | >95:5 | Cancer pain, migraine, appetite stimulation |
| Even ratio | 50:50 | Multiple sclerosis, spinal cord injury, peripheral neuropathy, other neurogenic pain. |
| Reverse/Broad ratio CBD | <25:75 | Rheumatoid arthritis, Inflammatory bowel diseases. |
| High CBD | <5:95 | Psychotic disorders (schizophrenia), Epilepsy & movement disorders Stroke, head injury, Disease modification in RA and other inflammatory conditions Appetite suppression |

Formulations containing specific, defined ratios of cannabinoids may be formulated from pure cannabinoids in combination with pharmaceutical carriers and excipients which are well-known to those skilled in the art. Pharmaceutical grade "pure" cannabinoids may be purchased from commercial suppliers, for example CBD and THC can be purchased from Sigma-Aldrich Company Ltd, Fancy Road, Poole Dorset, BH12 4QH, or may be chemically synthesised. Alternatively, cannabinoids may be extracted from Cannabis plants using techniques well-known to those skilled in the art.

In preferred embodiments of the invention the formulations comprise extracts of one or more varieties of whole Cannabis plants, particularly Cannabis sativa, Cannabis indica or plants which are the result of genetic crosses, self-crosses or hybrids thereof. The precise cannabinoid content of any particular cannabis variety may be qualitatively and quantitatively determined using methods well known to those skilled in the art, such as TLC or HPLC.

Thus, one may chose a Cannabis variety from which to prepare an extract which will produce the desired ratio of CBD to THC or CBDV to THCV or THCV to THC. Alternatively, extracts from two of more different varieties may be mixed or blended to produce a material with the preferred cannabinoid ratio for formulating into a pharmaceutical formulation.

The preparation of convenient ratios of THC- and CBD-containing medicines is made possible by the cultivation of specific chemovars of *cannabis*. These chemovars (plants distinguished by the cannabinoids produced, rather than the morphological characteristics of the plant) can be been bred by a variety of plant breeding techniques which will be familiar to a person skilled in the art. Propagation of the plants by cuttings for production material ensures that the genotype is fixed and that each crop of plants contains the cannabinoids in substantially the same ratio.

Furthermore, it has been found that by a process of horticultural selection, other chemovars expressing their cannabinoid content as predominantly tetrahydrocannabinovarin (THCV) or cannabidivarin (CBDV) can also be achieved.

Horticulturally, it is convenient to grow chemovars producing THC, THCV, CBD and CBDV as the predominant cannabinoid from cuttings. This ensures that the genotype in each crop is identical and the qualitative formulation (the proportion of each cannabinoid in the biomass) is the same. From these chemovars, extracts can be prepared by the similar method of extraction. Convenient methods of preparing primary extracts include maceration, percolation, extraction with solvents such as C1 to C5 alcohols (ethanol), Norflurane (HFA134a), HFA227 and liquid carbon dioxide under pressure. The primary extract may be further purified for example by supercritical or subcritical extraction, vaporisation and chromatography. When solvents such as those listed above are used, the resultant extract contains non-specific lipid-soluble material or "ballast". This can be removed by a variety of processes including chilling to −20° C. followed by filtration to remove waxy ballast, extraction with liquid carbon dioxide and by distillation. Preferred plant cultivation and extract preparation methods are shown in the Examples. The resulting extract is suitable for incorporation into pharmaceutical preparations.

There are a number of therapeutic conditions which may be treated effectively by *cannabis*, including, for example, cancer pain, migraine, appetite stimulation, multiple sclerosis, spinal cord injury, peripheral neuropathy, other neurogenic pain, rheumatoid arthritis, inflammatory bowel diseases, psychotic disorders (schizophrenia), epilepsy & movement disorders, stroke, head injury, appetite suppression. The proportion of different cannabinoids in a given formulation determines the specific therapeutic conditions which are best treated (as summarised in Table 2, and stated in the accompanying claims).

The principles of formulation suitable for administration of *cannabis* extracts and cannabinoids can also be applied to other medicaments such as alkaloids, bases and acids. The requirements are that, if the medicament is insoluble in saliva, it should be solubilised and/or brought into the appropriate unionised form by addition of buffering salts and pH adjustment.

Other lipophilic medicaments which may be included in the general formulations of the invention may include, but are not limited to, morphine, pethidine, codeine, methadone, diamorphine, fentanyl, alfentanil, buprenorphine, temazepam, lipophilic analgesics and drugs of abuse. The term "drugs of abuse" encompasses compounds which may produce dependence in a human subject, typically such compounds will be analgesics, usually opiates or synthetic derivatives thereof.

The formulation is preferably packaged in a glass vial. It is preferably filled to a slight over-pressure in an inert atmosphere e.g. nitrogen to prevent/slow oxidative breakdown of the cannabinoids, and is contained in a form such that ingress of light is prevented, thereby preventing photochemical degradation of the cannabinoids. This is most effectively achieved using an amber vial, since the applicant has determined that it is UV and light in the blue spectrum, typically in the wavelength range 200-500 nm, that is responsible for photodegradation.

The invention will be further described, by way of example only, with reference to the following experimental data and exemplary formulations, together with the accompanying Figures:

BRIEF DESCRIPTION OF THE DRAWINGS

FIG. 2 illustrates mean plasma concentrations of cannabinoids CBD, THC and 11-hydroxy THC following administration of a *cannabis* extract containing a 1:1 ratio of THC:CBD to a human subject.

FIG. 5 illustrates cross-sectional area of aerosol plume vs viscosity for propylene glycol/ethanol liquid spray formulations.

FIGS. 6 and 6*a* show results of HPLC analysis of samples drawn from stored, light exposed solutions of THC, before and after charcoal treatment.

FIGS. 7 and 7*a* show results of HPLC analysis of samples drawn from stored, light exposed solutions of CBD, before and after charcoal treatment.

DETAILED DESCRIPTION OF THE INVENTION

Development of Pump-Action Spray Formulations

Figure 1A:
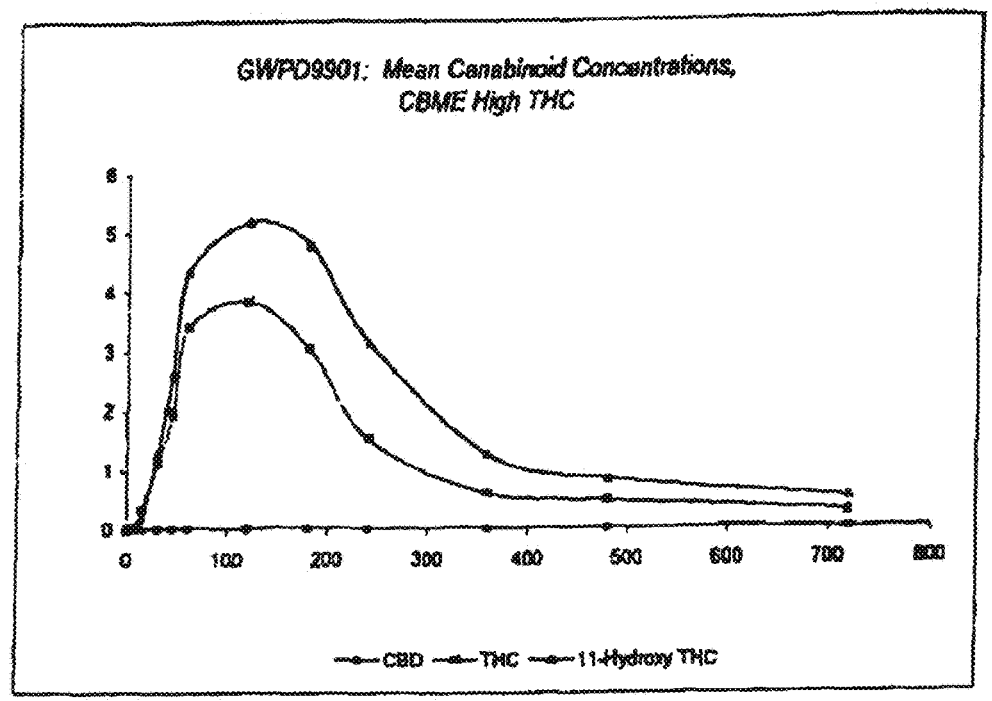
FIGS. 1*a* and 1*b* illustrate mean plasma concentrations of cannabinoids CBD, THC and 11-hydroxy THC following administration of high CBD (FIG. 1*a*) and high THC (FIG. 1*b*) *cannabis* extracts to human subjects.

Initially the applicant looked at cannabinoid uptake in patients by applying drops sublingually (BDS dissolved in a mixture of a glycerol/propylene glycol and ethanol) THC 5 mg/ml, CBD 5 mg/ml and THC/CBD 5 mg/ml plus 5 mg/ml. The results are noted in Table 3 below:

TABLE 3

Initial absorption: 20 min
T max: approx 2 hours
C max: 6 ng/ml THC, 2 ng/ml CBD
AUC 0-12: approx 16 ng · h/ml THC, 8 ng · h/ml
CBD following a dose of approx 20 mg of each cannabinoids
Plasma levels after 6 hours were about 1 ng/ml THC and 0.5 ng/ml CBD The proportion of 11 hydroxy tetrahydro cannabinol to THC (AUC 0-12) was about 1.9 indicating a significant amount of oral ingestion may have occurred.

On moving to a pump action sublingual spray (following problems solubilising cannabinoids with hydroflurocabon propellant systems) the applicant obtained the results noted in Table 4. The solvent system comprised 50:50 ethanol to propylene glycol (v/v ratio) with THC 25 mg/ml; CBD 50 mg/ml and THC/CBD 25 mg/ml plus 50 mg/ml respectively.

TABLE 4

Initial absorption: 60 min
T max: approx 3 hours
C max: 6 ng/ml THC, 8 ng/ml CBD
AUC 0-12: approx 16 ng · h/ml THC, 22 ng · h/ml
CBD following a dose of approx 21 mg of THC and 35 mg CBD
Plasma levels after 6 hours were about 1 ng/ml THC and 1 ng/ml CBD The proportion of 11 hydroxy tetrahydro cannabinol to THC (AUC 0-12) was about 1.6. The profile for each cannabinoid was similar irrespective of the formulation (THC, CBD, THC plus CBD).

After accounting for the different dosages, whilst the extent of absorption was comparable to the drops, the rate of absorption was slower and the proportion metabolised reduced.

Despite the slower rate of absorption the pump spray mechanism and the ethanol/propylene glycol carrier system provided the opportunity to administer sufficient cannabinoids, in a flexible dose form with accuracy and advantageously with reduced metabolism.

Figure 1B:
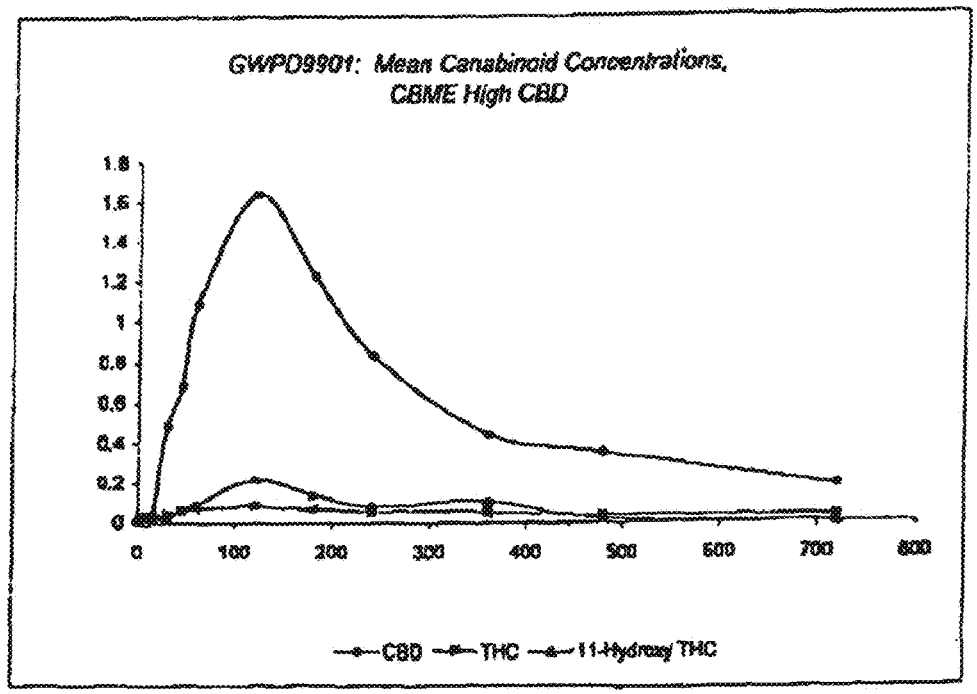

The data obtained is illustrated in FIGS. 1a, 1b and 2, which show the mean plasma concentrations for the formulations identified with reference to Tables 3 and 4.

That effective delivery of the cannabinoids can be achieved in a vehicle consisting of ethanol and propylene glycol is illustrated by the plasma levels shown in FIGS. 1a, 1b and 2. These show, respectively, formulations containing the high THC and high CBD formulations in FIGS. 1a and 1b. Similarly, the effectiveness of a defined ratio formulation THC:CBD 1:1 is illustrated in FIG. 2.

Significantly the ethanol/propylene glycol system was found to only work with a pump action spray within quite narrow limits.

The findings giving rise to the development of pump spray formulations, as exemplified in formulations 1-4 below, are set out below:

Example 1—Significance of Particle Size

Applicant observed that the propellant aerosols that were developed suffered from "bounce back" and this appeared to be a function of delivery speed and particle size.

Applicant determined that, in contrast to the propellant driven system, a pump spray could deliver an aerosol plume in which the particle size could be controlled to generate a particle size of between 20 and 40 microns (thus maximising the amount of material hitting the sublingual/buccal mucosa and thus the amount of cannabinoids that can be absorbed). To produce particles of the appropriate size the viscosity of the formulation needed to be carefully controlled. If the formulation was too viscous droplet formation was hindered, a jet formed and the valve blocked; If the formulation was not viscous enough they got excessive nebulisation, a plume of broad cross sectional area formed, and the spray was no longer directed solely onto the sublingual/buccal mucosa. This could result in the formulation pooling and some of the formulation being swallowed. In both cases the result is unsatisfactory.

In fact, it turned out that for the solvent of preferred choice, ethanol, and the co-solvent of preferred choice, propylene glycol, the working range was fairly narrow as demonstrated below:

The viscosity of different combinations of ethanol/propylene glycol were studied and their spray performance with a vp7/100 valve (Valois) compared. The results are tabulated in Table 5 below:

TABLE 5

| Propylene glycol/ethanol | Relative viscosity (run time in sec) | Spray performance |
| --- | --- | --- |
| 100/0 | 442 | Jet formed |
| 80/20 | 160 | Jet formed |
| 60/40 | 80 | Some jetting |
| 50/50 | 62 | Good aerosol plume |
| 40/60 | 44 | Good aerosol plume |
| 20/80 | 26 | Good aerosol plume |
| 0/100 | 16 | Good aerosol plume |

From this data it appeared that addition of propylene glycol at greater than 60/40 would not be acceptable. These result, when read alongside U.S. Pat. No. 3,560,625, could have suggested that the said solvent/co-solvent combination would be no good. However, applicant found that patients could tolerate ethanol levels of this order when presented in the given formulations.

The effect of viscosity on aerosol plume was quantified by spraying the various formulations at a standard distance of 0.5 cm onto disclosing paper. The distance represents the typical distance between the nozzle of the pump action spray unit and the sub lingual cavity in normal use. The paper was photocopied and the image of the plume excised and weighed to give a relative cross sectional area. The relative value was then converted into a real cross sectional area by dividing this value by the weight per $cm^2$ of the photocopier paper (determined by weighing a known area of paper). The results are given in Table 6 below:

TABLE 6

| Propylene glycol/ethanol | Area of cross section of spray plume |
| --- | --- |
| 100/0 | 3.5 $cm^2$ |
| 80/20 | 14.2 $cm^2$ |
| 60/40 | 17.9 $cm^2$ |
| 50/50 | 20.7 $cm^2$ |
| 40/60 | 29.4 $cm^2$ |
| 20/80 | 54.4 $cm^2$ |
| 0/100 | 93.8 $cm^2$ |

Figure 3:
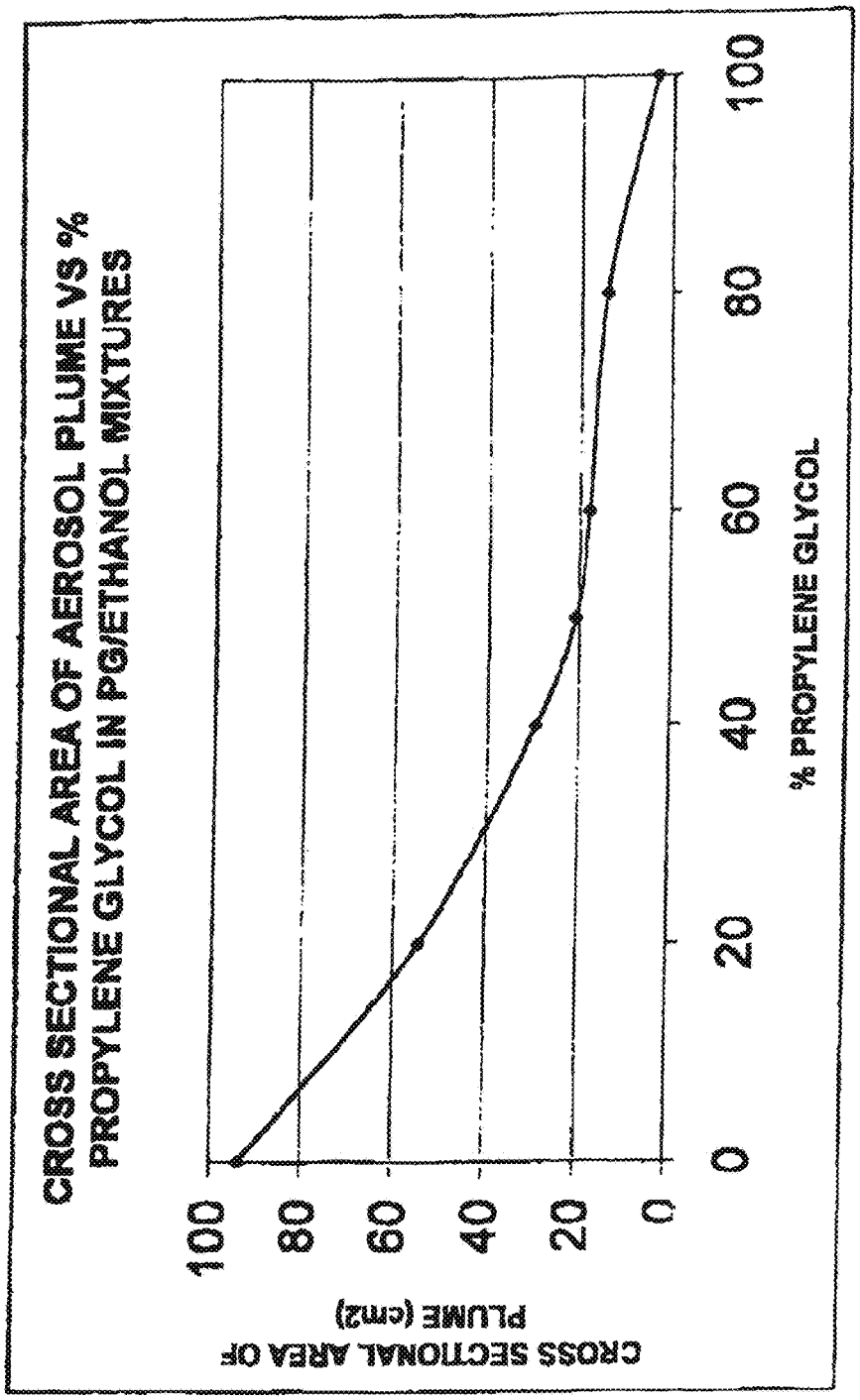
FIG. 3 illustrates cross-sectional area of aerosol plume vs % propylene glycol in propylene glycol/ethanol liquid spray formulations.

This data is illustrated in FIG. 3.

Figure 4:
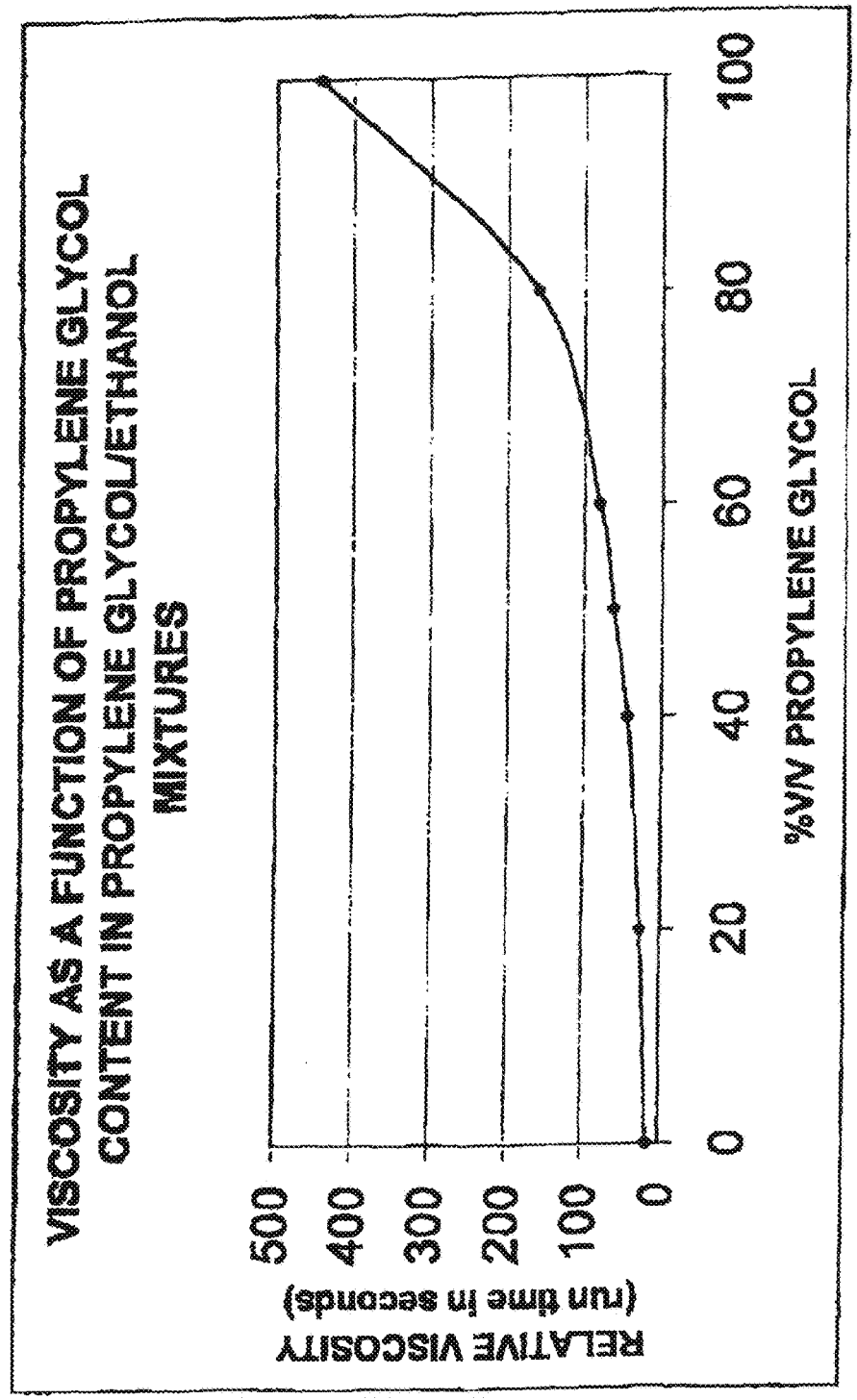
FIG. 4 illustrates viscosity as a function of propylene glycol content in propylene glycol/ethanol liquid spray formulations.

Additionally plots of viscosity of mixtures of ethanol and propylene glycol content FIG. 4 and plume cross section as a function of viscosity FIG. 5 are given.

The figures emphasise the dramatic and undesirable changes in properties which occur outside the narrow range of ethanol/propylene glycol wt/wt of 60/40 and 40/60, and more particularly still 55/45 to 45/55, most preferably about 50/50.

Other factors are also significant in ensuring the combination is used in a narrow range. Increasing the ethanol levels beyond 60 vol % gives rise to irritation and at propylene glycol levels approaching 60% and as low as 55%, in the case of BDS, non polar derivatives present in the BDS begin to precipitate out on prolonged ambient storage.

Other co-solvents which might be used would be expected to have similar limitations. The more viscous the co-solvent the greater the problem of producing a plume forming spray, and the more polar, the greater the risk that precipitation will be exacerbated.

However, because the combination of ethanol/propylene glycol is able to dissolve up to 50 mg/ml (i.e. therapeutically desirable levels of cannabinoids), is non irritating, pharmaceutically acceptable, and the propylene glycol also acts as a penetration enhancer maximising bioavailability of the cannabinoids it is particularly advantageous.

The mean particle size of the preferred compositions have been shown to be 33 μm when tested using a Malvern Marsteriser. The droplets, which are considerably greater than 5 μm, therefore minimise the risk of inhalation of aerosol.

Example 2—Effect of Water when the Cannabinoids are Present in a BDS

The presence of greater than 5% water in the formulation was shown to cause precipitation of the BDS as illustrated by the investigation described in Table 7 below:

TABLE 7

Sequential addition of water was made to 5 ml 25 mg/ml THC and 5 ml 25 mg/ml CBD in an ethanol/propylene glycol formulate (50/50).

| Vol of water added ml | Final vol ml | Approx final solvent ratio % vol Water/propylene glycol/ethanol | observation |
|---|---|---|---|
| 0 | 5 | 0/50/50 | Solution |
| 0.05 | 5.05 | 1/49.5/49.5 | Ppt forms but re dissolves on mixing |
| 0.21 | 5.26 | 5/47.5/47.5 | Ppt forms. Solution remains cloudy after mixing |

Indeed because of this observation the use of anhydrous ethanol is preferred.

Example formulations (non-limiting) according to the invention are as follows:

COMPOSITION 1 (General)

| COMPONENT | AMOUNT PER UNIT (1 ml) | FUNCTION |
|---|---|---|
| Active | | |
| THC (BDS) | 25-50 mg/ml | Active |
| CBD (BDS) | 25-50 mg/ml | |
| Excipient | | |
| Propylene Glycol | 0.5 ml/ml | Co solvent |
| Peppermint oil | 0.0005 ml/ml | Flavour |
| Ethanol (anhydrous) | qs to 1 ml | Solvent |

COMPOSITION 2 (High THC)

| COMPONENT | AMOUNT PER UNIT (1 ml) | FUNCTION |
|---|---|---|
| Active | | |
| THC (BDS) | 25 mg/ml | Active |
| Excipient | | |
| Propylene Glycol | 0.5 ml/ml | Co solvent |
| Peppermint oil | 0.0005 ml/ml | Flavour |
| Ethanol (anhydrous) | qs to 1 ml | Solvent |

COMPOSITION 3 (High CBD)

| COMPONENT | AMOUNT PER UNIT (1 ml) | FUNCTION |
|---|---|---|
| Active | | |
| CBD (BDS) | 25 mg/ml | Active |
| Excipient | | |
| Propylene Glycol | 0.5 ml/ml | Co solvent |
| Peppermint oil | 0.0005 ml/ml | Flavour |
| Ethanol (anhydrous) | qs to 1 ml | Solvent |

COMPOSITION 4 (THC/CBD Substantially 1:1)

| COMPONENT | AMOUNT PER UNIT (1 ml) | FUNCTION |
|---|---|---|
| Active | | |
| THC (BDS) | 25 mg/ml | Active |
| CBD (BDS) | 25 mg/ml | Active |
| Excipient | | |
| Propylene Glycol | 0.5 ml/ml | Co solvent |
| Peppermint oil | 0.0005 ml/ml | Flavour |
| Ethanol (anhydrous) | qs to 1 ml | Solvent |

Example 3

The following example illustrates the application of liquid spray formulations to the buccal mucosae and the blood levels produced by buccal absorption in comparison with sublingual administration.

The following liquid formulations suitable for buccal administration contain self-emulsifying agents, and hence do not fall within the scope of the present invention. Nevertheless, the general principles illustrated by use of these compositions applies equally to the delivery formulations according to the invention. Solutions were produced by dissolving (at a temperature not exceeding 50° C.) the following ingredients (quantitative details are expressed as parts by weight):—

| | A | B | C | D | E |
|---|---|---|---|---|---|
| Glyceryl monostearate (self-emulsifying) | 2 | — | 2 | — | 2 |
| Glyceryl monooleate (self-emulsifying) | — | 2 | — | 2 | — |
| Cremophor RH40 | 20 | 30 | 30 | 20 | 30 |
| CBME-G1 to give THC | 5 | 10 | — | — | — |
| CBME-G5 to give CBD | — | — | 5 | 10 | — |
| CBME-G1 and G5 to give THC & CBD | — | — | — | — | 10 each |
| α-Tocopherol | 0.1 | 0.1 | 0.1 | 0.1 | 0.1 |
| Ascorbyl palmitate | 0.1 | 0.1 | 0.1 | 0.1 | 0.1 |
| Ethanol BP to produce | 100 | 100 | 100 | 100 | 100 |

*Cannabis* Based Medicine Extract (CBME) is an extract of *cannabis* which may be prepared by, for example, percolation with liquid carbon dioxide, with the removal of ballast by cooling a concentrated ethanolic solution to a temperature of −20° C. and removing precipitated inert plant constituents by filtration or centrifugation.

The product formed by mixing these ingredients is dispensed in 6 ml quantities into a glass vial and closed with a pump action spray. In use, the dose is discharged through a break-up button or conventional design. Proprietary devices that are suitable for this purpose are Type VP7 produced by Valois, but similar designs are available from other manufacturers. The vial may be enclosed in secondary packaging to allow the spray to be directed to a particular area of buccal mucosa. Alternatively, a proprietary button with an extension may be used to direct the spray to a preferred area of buccal mucosa.

Each 1 ml of product contains 50-100 mg of $\Delta^9$-tetrahydrocannabinol (THC) and/or cannabidiol (CBD). Each actuation of the pump delivers a spray which can be directed to the buccal mucosae. In the above formulations CBMEs of known cannabinoid strength are used. CBME-G1 is an extract from a high THC-yielding strain of *cannabis*, and CBME-G5 is from a high CBD-yielding variety. It will be clear to a person skilled in the art that purified cannabinoids, and extracts containing the cannabinoids, can be made formulated as described above by quantitative adjustment.

Although solutions of CBME in ethanol alone can be used as a spray, the quantity of cannabinoid that can be delivered is limited by the aggressive nature of pure ethanol in high concentration as a solvent. This limits the amount that can be applied to the mucosae without producing discomfort to the patient. When a group of patients received THC or CBD in a solution of the type described above, directing the spray either sublingually or against the buccal mucosa, the patients uniformly reported a stinging sensation with the sublingual application, but mild or no discomfort when the same solution was sprayed onto the buccal mucosa. Spraying small quantities of this type of formulation onto the buccal mucosa does not appreciably stimulate the swallowing reflex. This provides greater dwell time for the formulation to be in contact with the buccal surface.

Formulations were administered to a group of 13 human subjects so that they received 4 mg THC, 4 mg of CBD or placebo (vehicle alone) via a sublingual tablet, sublingual pump-action spray or buccal route.

Absorption [area under the absorption curve (AUC)] of cannabinoid and primary metabolite were determined in samples of blood taken after dosing. The following Table 8 gives these as normalised mean values.

TABLE 8

| | Route of Administration | | |
|---|---|---|---|
| Analyte in Plasma | PAS sublingual AUC | Sublingual tablet AUC | Oropharyngeal AUC |
| THC | 2158.1 | 1648.4 | 1575 |
| 11-OH THC | 3097.6 | 3560.5 | 2601.1 |
| CBD | 912 | 886.1 | 858 |

These results show that the total amounts of cannabinoid absorbed by sublingual and buccal (oropharyngeal) routes are similar but that there is a substantial (approximately 25%) reduction in the amount of 11-hydroxy (11-OH) metabolite detected after oropharyngeal (buccal) administration. This finding is not inconsistent with reduced swallowing (and subsequent reduced hepatic) metabolism of the buccal formulation.

It is known that the 11-hydroxy metabolite of THC (11-OH THC) is possibly more psychoactive than the parent compound. It is therefore desirable to minimise the amount of this metabolite during administration, and this is likely to be achieved by using a formulation and method of application which reduces the amount of a buccal or sublingual dose that is swallowed. The pump action spray appears to offer a simple means of reducing the amount of material that is swallowed and metabolised by absorption from the intestinal tract below the level of the oropharynx.

Example 4—Growing of Medicinal *Cannabis*

Plants are grown as clones from germinated seed, under glass at a temperature of 25° C.±1.5° C. for 3 weeks in 24 hour daylight; this keeps the plants in a vegetative state. Flowering is induced by exposure to 12 hour day length for 8-9 weeks.

No artificial pesticides, herbicides, insecticides or fumigants are used. Plants are grown organically, with biological control of insect pests.

Figure 8:
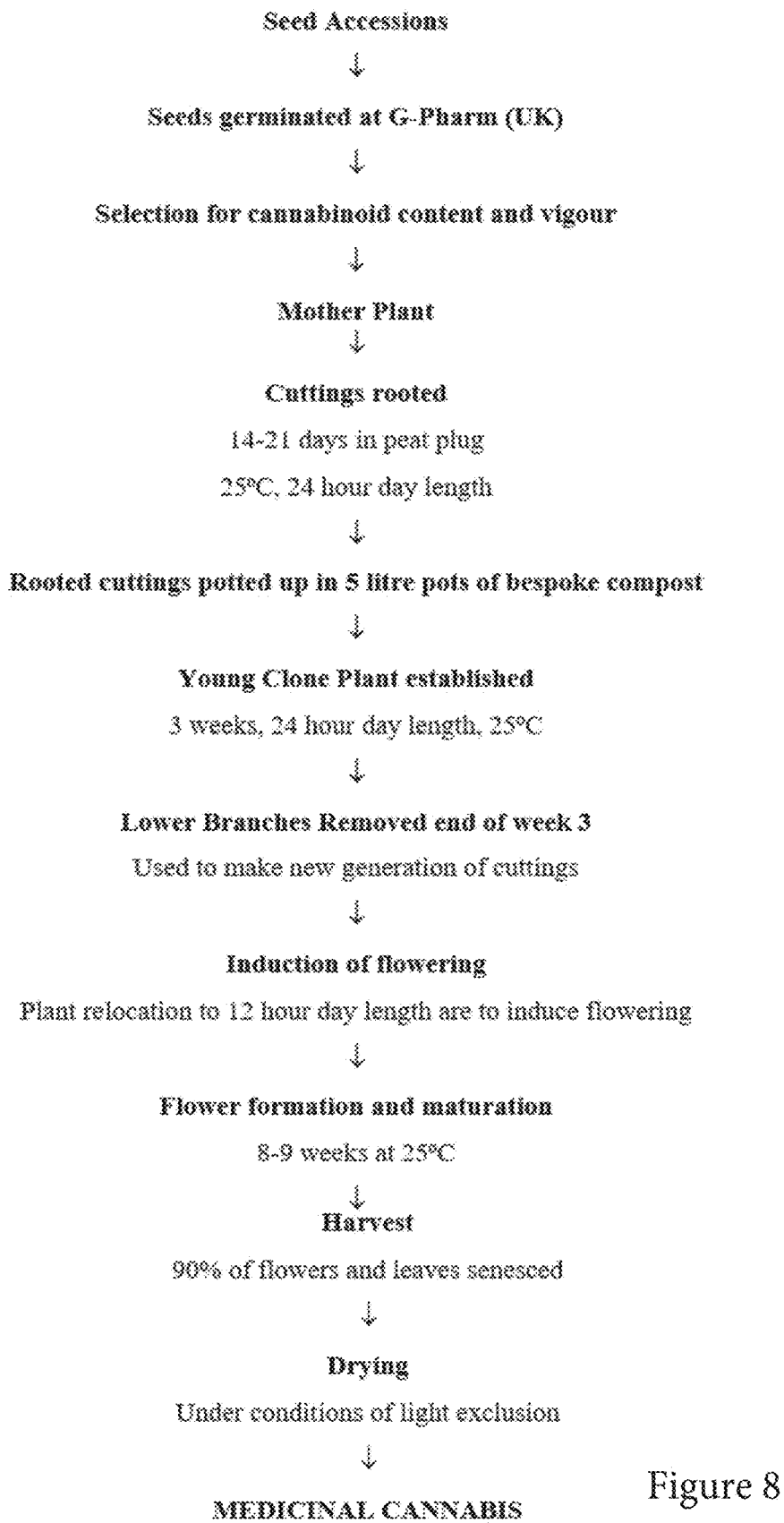
FIG. 8 shows a summary of steps in production from seed accession to dried Medicinal *Cannabis*.

The essential steps in production from seed accession to dried Medicinal *Cannabis* are summarised in FIG. 8.

Example 5—Determination of Cannabinoid Content in Plants and Extracts

Identity by TLC
a) Materials and Methods
Equipment Application device capable of delivering an accurately controlled volume of solution i.e., 1 μl capillary pipette or micro liter syringe.
TLC development tank with lid
Hot air blower
Silica gel G TLC plates (SIL N-HR/UV254), 200 μm layer with fluorescent indicator on polyester support.
Dipping tank for visualisation reagent.
Mobile phase 80% petroleum ether 60:80/20% Diethyl ether.
Visualisation reagent 0.1% w/v aqueous Fast Blue B (100 mg in 100 ml de-ionised water). An optional method is to scan at UV 254 and 365 nm.
b) Sample Preparation
   i) Herbal raw material
   Approximately 200 mg of finely ground, dried *cannabis* is weighed into a 10 ml volumetric flask. Make up to volume using methanol:chloroform (9:1) extraction solvent.
   Extract by ultrasound for 15 minutes. Decant supernatant and use directly for chromatography.
   ii) Herbal drug Extract
   Approximately 50 mg of extract is weighed into a 25 ml volumetric flask. Make up to volume using methanol solvent. Shake vigorously to dissolve and then use directly for chromatography.
c) Standards
0.1 mg/ml delta-9-THC in methanol.
0.1 mg/ml CBD in methanol.
The standard solutions are stored frozen at −20° C. between uses and are used for up to 12 months after initial preparation.
d) Test Solutions and Method
   Apply to points separated by a minimum of 10 mm.
   i) either 5 μl of herb extract or 1 μl of herbal extract solution as appropriate,
   ii) 10 μl of 0.1 mg/ml delta-9-THC in methanol standard solution, iii) 10 µl of 0.1 mg/ml CBD in methanol standard solution.

Elute the TLC plate through a distance of 8 cm, then remove the plate. Allow solvent to evaporate from the plate and then repeat the elution for a second time (double development).

The plate is briefly immersed in the Fast Blue B reagent until the characteristic re/orange colour of cannabinoids begins to develop. The plate is removed and allowed to dry under ambient conditions in the dark.

A permanent record of the result is made either by reproduction of the image by digital scanner (preferred option) or by noting spot positions and colours on a tracing paper.

Assay THC, THCA, CBD, CBDA and CBN by HPLC a) Materials and Methods

Equipment: HP 1100 HPLC with diode array detector and autosampler. The equipment is set up and operated in accordance with in-house standard operating procedures (SOPlab037)

HPLC column Discovery C8 5 µm, 15×0.46 cm plus Kingsorb ODS2 precolumn 5 µm 3×0.46 cm.

Mobile Phase Acetonotrile:methanol:0.25% aqueous acetic acid (16:7:6 by volume)

Column Operating 25° C.

Temperature

Flow Rate 1.0 ml/min

Injection Volume 10 µl

Run time 25 mins

Detection Neutral and acid cannabinoids 220 nm (band width 16 nm) Reference wavelength 400 nm/bandwidth 16 nm Slit 4 nm Acid cannabinoids are routinely monitored at 310 nm (band width 16 nm) for qualitative confirmatory and identification purposes only.

Data capture HP Chemistation with Version A7.01 software b) Sample Preparation

Approximately 40 mg of *Cannabis* Based Medicinal Extract is dissolved in 25 ml methanol and this solution is diluted to 1 to 10 in methanol. This dilution is used for chromatography.

0.5 ml of the fill solution, contained within the Pump Action Sublingual Spray unit, is sampled by glass pipette. The solution is diluted into a 25 ml flask and made to the mark with methanol. 200 µl of this solution is diluted with 800 µl of methanol.

Herb or resin samples are prepared by taking a 100 mg sample and treating this with 5 or 10 ml of Methanol/Chloroform (9/1 w/v). The dispersion is sonicated in a sealed tube for 10 minutes, allowed to cool and an aliquot is centrifuged and suitably diluted with methanol prior to chromatography.

c) Standards

External standardisation is used for this method. Dilution of stock standards of THC, CBD and CBN in methanol or ethanol are made to give final working standards of approximately accurately 0.1 mg/ml. The working standards are stored at −20° C. and are used for up to 12 months after initial preparation.

Injection of each standard is made in triplicate prior to the injection of any test solution. At suitable intervals during the processing of test solutions, repeat injections of standards are made. In the absence of reliable CBDA and THCA standards, these compounds are analysed using respectively the CBD and THC standard response factors.

The elution order has been determined as CBD, CBDA, CBN, THC and THCA. Other cannabinoids are detected using this method and may be identified and determined as necessary.

d) Test Solutions

Diluted test solutions are made up in methanol and should contain analytes in the linear working range of 0.02-0.2 mg/ml.

e) Chromatography Acceptance Criteria:

The following acceptance criteria are applied to the results of each sequence as they have been found to result in adequate resolution of all analytes (including the two most closely eluting analytes CBD and CBDA)

i) Retention time windows for each analyte:
CBD 5.4-5.9 minutes
CBN 7.9-8.7 minutes
THC 9.6-10.6 minutes ii) Peak shape (symmetry factor according to BP method)
CBD <1.30
CBN <1.25
THC <1.35 iii) A number of modifications to the standard method have been developed to deal with those samples which contain late eluting impurity peaks e.g., method CBD2A extends the run time to 50 minutes. All solutions should be clarified by centrifugation before being transferred into autosampler vials sealed with teflon faced septum seal and cap.

iv) The precolumn is critical to the quality of the chromatography and should be changed when the back pressure rises above 71 bar and/or acceptance criteria regarding retention time and resolution, fall outside their specified limits.

f) Data Processing

Cannabinoids can be subdivided into neutral and acidic—the qualitative identification can be performed using the DAD dual wavelength mode. Acidic cannabinoids absorb strongly in the region of 220 nm-310 nm. Neutral cannabinoids only absorb strongly in the region of 220 nm.

Routinely, only the data recorded at 220 nm is used for quantitative analysis.

The DAD can also be set up to take UV spectral scans of each peak, which can then be stored in a spectral library and used for identification purposes.

Data processing for quantitation utilises batch processing software on the Hewlett Packard Chemstation.

a) Sample Chromatograms

HPLC sample chromatograms for THC and CBD Herbal Drug extracts are provided in the accompanying Figures.

Example 6—Preparation of the Herbal Drug Extract

Figure 9:
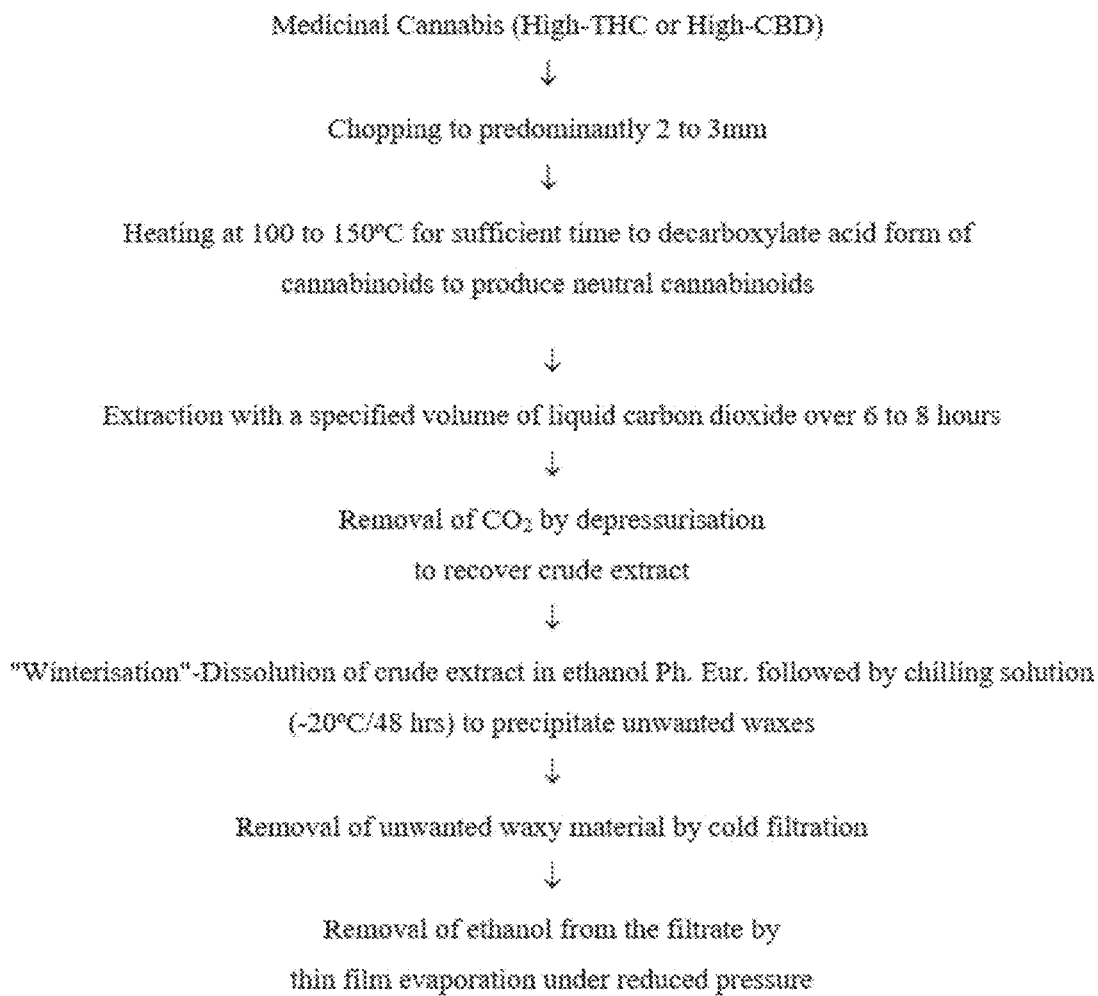
FIG. 9 shows a flow chart of the process of manufacturing extract from the High-THC and High-CBD chemovars.

A flow chart showing the process of manufacture of extract from the High-THC and High-CBD chemovars is given in FIG. 9.

The resulting extract is referred to as a *Cannabis* Based Medicine Extract and is also classified as a Botanic Drug Substance, according to the US Food and Drug Administration Guidance for Industry Botanical Drug Products.

Example 7

High THC *cannabis* was grown under glass at a mean temperature of 21+2° C., RH 50-60%. Herb was harvested and dried at ambient room temperature at a RH of 40-45% in the dark. When dry, the leaf and flower head were stripped from stem and this dried biomass is referred to as "medicinal *cannabis*".

Medicinal *cannabis* was reduced to a coarse powder (particles passing through a 3 mm mesh) and packed into the chamber of a Supercritical Fluid Extractor. Packing density was 0.3 and liquid carbon dioxide at a pressure of 600 bar was passed through the mass at a temperature of 35° C. Supercritical extraction is carried out for 4 hours and the extract was recovered by stepwise decompression into a collection vessel. The resulting green-brown oily resinous extract is further purified. When dissolved in ethanol BP (2 parts) and subjected to a temperature of −20° C. for 24 hours a deposit (consisting of fat-soluble, waxy material) was thrown out of solution and was removed by filtration. Solvent was removed at low pressure in a rotary evaporator. The resulting extract is a soft extract which contains approximately 60% THC and approximately 6% of other cannabinoids of which 1-2% is cannabidiol and the remainder is minor cannabinoids including cannabinol. Quantitative yield was 9% w/w based on weight of dry medicinal *cannabis*.

A high CBD chemovar was similarly treated and yielded an extract containing approximately 60% CBD with up to 4% tetrahydrocannabinol, within a total of other cannabinoids of 6%. Extracts were made using THCV and CBDV chemovars using the general method described above.

A person skilled in the art will appreciate that other combinations of temperature and pressure (e.g. in the range +10° C. to 35° C. and 60-600 bar) can be used to prepare extracts under supercritical and subcritical conditions.

Example 8—The Effects of Light on the Stability of the Alcoholic Solutions of THC, CBD or THCV The following example includes data to support the packaging of liquid dosage forms in amber glass, to provide some protection from the degradative effects of light on cannabinoids.

Further credence is also given to the selection of the lowest possible storage temperature for the solutions containing cannabinoid active ingredients.

Background and Overview:

Light is known to be an initiator of degradation reactions in many substances, including cannabinoids. This knowledge has been used in the selection of the packaging for liquid formulations, amber glass being widely used in pharmaceutical presentations as a light exclusive barrier.

Experiments were set up to follow the effects of white light on the stability of methanolic solutions of THC, CBD or THCV. Following preliminary knowledge that light of different wavelengths may have differing effects on compound stability (viz. tretinoin is stable only in red light or darkness), samples were wrapped in coloured acetate films or in light exclusive foil. A concurrent experiment used charcoal treated CBME to study the effects of the removal of plant pigments on the degradation process.

Materials and Methods:

Cannabinoids: 1 mg/ml solutions of CBME were made up in AR methanol. Methanolic solutions of CBME (100 mg/ml) were passed through charcoal columns (Biotage Flash 12AC 7.5 cm cartridges, b/no. 273012S) and were then diluted to 1 mg/ml. Solutions were stored in soda-glass vials, which were tightly screw capped and oversealed with stretch film. Tubes were wrapped in coloured acetate films as follows:

Red, Yellow, Green, and Cyan

Solutions were also filled into the amber glass U-save vials; these were sealed with a septum and oversealed. One tube of each series of samples was tightly wrapped in aluminium foil in order to completely exclude light. This served as a "dark" control to monitor the contribution of ambient temperature to the degradation behaviour. All of the above tubes were placed in a box fitted with 2×40 watt white Osram fluorescent tubes. The walls of the box were lined with reflective foil and the internal temperature was monitored at frequent intervals.

A further tube of each series was stored at −20° C. to act as a pseudo to the reference sample; in addition, one tube was exposed directly to light without protection. Samples were withdrawn for chromatographic analysis at intervals up to 112 days following the start of the study. The study was designated AS01201/AX282.

Samples of the test solutions were withdrawn and diluted as appropriate for HPLC and TLC analysis. HPLC was carried out in accordance with TM GE.004.V1 (SOPam058). TLC was performed on layers on Silica gel (MN SilG/UV) in accordance with TM GE.002.V1 (SOPam056). Two further TLC systems were utilised in order to separate degradation products:

a) SilG/UV, stationary phase, hexane/acetone 8/2 v/v mobile phase b) RPC18 stationary phase, acetonitrile/methanol/0.25% aqueous acetic acid 16/7/6 by volume Visualisation of cannabinoids was by Fast Blue B salt.

Results and Discussion:

HPLC Quantitative Analysis:

The results from the HPLC analysis of samples drawn from the stored, light exposed solutions, are plotted and presented as FIGS. 6 and 6*a* (THC before and after charcoal treatment), and FIGS. 7 and 7*a* (CBD before and after charcoal treatment).

It can be seen from FIGS. 6 and 6*a* that there are significant improvements to the stability of THC in all solutions, except those stored in the dark (at ambient temperature) and at −20° C. (and hence which are not under photochemical stress). Even storage in amber glass shows an improvement when un-treated extract is compared with charcoal treated extract. This, however, may reflect in an improvement of the thermal stability of the charcoal treated extract.

FIGS. 7 and 7*a* present similar data for CBD containing extracts, from which it can be seen that this cannabinoid is significantly more sensitive to the effects of light than is THC. In the absence of charcoal, all exposures, except in amber glass, light excluded (foil) and −20° storage, had degraded to non-detectable levels of CBD before 40 days. This improved to figures of between 42 and 62 days following charcoal treatment. Amber glass protected CBD showed an improvement from ~38% residual compound at 112 days without charcoal clean up, to approximately 64% at the same time after charcoal treatment. There was also an improvement in the stability of CBD in light excluded solution after charcoal treatment. This can only reflect a reduction in either thermo-oxidative degradation, or a residual photochemical degradation initiated by light (and/or air) during CBME and solution preparation.

Thin Layer Chromatography Qualitative Analysis:

The evaluation of the light degraded solutions using thin layer chromatography, used both the existing normal phase system (i.e. Silica stationary phase and hexane/diethyl ether as mobile phase) and two additional systems, capable of resolving more polar or polymeric products formed during the degradation processes.

Thus, chromatography using the hexane/diethyl ether system, showed that for THC by day 112, there was a reduction in the intensity of the THC and secondary CBD spots with all of the colour filtered lights (data not shown). At the same time, there was an increase in the intensity of Fast Blue B staining material running at, or close to, the origin. Foil protected solution exhibited none of these effects.

CONCLUSIONS AND RECOMMENDATIONS

Cannabinoids are known to be degraded by a number of natural challenges, viz. light, heat, oxygen, enzymes etc. It is most likely that in an extract of herbal plant material, which has not been subjected to extensive clean-up procedures, that some of these processes may still be able to continue. Paradoxically, it is also likely that the removal of cannabinoids from the presence of any protection agents within the plant tissue, may render the extract more likely to suffer from particular degradation pathways.

Packaging into amber glass vials, conducting formulation manufacture in amber filtered light, and the storage of plant extracts and pharmaceutical formulations at temperatures as low as possible compatible with manufacturing and distribution requirements and patient compliance eliminates, or at least reduces, the effect of light on degradation of cannabinoids. These actions dramatically improved the storage stability of both plant extracts and finished products.

It was interesting to note that CBD appeared to be markedly less stable than THC, when subjected to photochemical stress. This is the opposite of the finding for the relative thermo-oxidative stabilities, in which THC is the less stable. This seems to indicate that, although polymeric degradation products may be the common result of both photochemical and thermo-oxidative degradation, the exact details of the mechanism are not identical for the two processes.

Among the conclusions that can be drawn are the following:
1] The choice of amber glass for the packaging of the dose solutions provides improved stability, but minor improvements can be made by additional light exclusion measures.
2] The drying process and subsequent extraction and formulation of *cannabis* extracts should indeed be carried out in low intensity, amber filtered light.
3] Consideration should be given to the blanketing of extracts under an inert atmosphere (e.g. Nitrogen).
4] Clean-up of *cannabis* extracts by simple charcoal filtration after winterisation, may yield substantial improvements to product shelf-life.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

The invention claimed is:

1. A cannabinoid containing pharmaceutical formulation, wherein the formulation comprises one or more cannabinoids and one or more pharmaceutically acceptable excipients is packaged in packaging to improve storage stability by protecting the formulation from the degradation by light, wherein the packaging comprises a light-excluding foil, and wherein the pharmaceutical formulation comprises an alcoholic solvent.

2. The cannabinoid containing pharmaceutical formulation as claimed in claim 1, wherein the formulation comprises one or more of the cannabinoids selected from tetrahydrocannabinol (THC), cannabidiol (CBD), tetrahydrocannabivarin (THCV) and cannabidivarin (CBDV).

3. The cannabinoid containing pharmaceutical formulation as claimed in claim 2, wherein the formulation comprises cannabidiol (CBD).

4. The cannabinoid containing pharmaceutical formulation as claimed in claim 1, wherein the formulation is packaged so as to prevent ingress of light.

5. The cannabinoid containing pharmaceutical formulation as claimed in claim 1, wherein the formulation is packaged to exclude UV light and/or light from the blue region of the spectrum.

6. The cannabinoid containing pharmaceutical formulation as claimed in claim 5, wherein the formulation is packaged to exclude the wavelength of light between 200 and 500 nm.

7. The cannabinoid containing pharmaceutical formulation as claimed in claim 1, wherein the cannabinoid is present as an extract or a highly purified Pharmacopeial grade substance.

8. The cannabinoid containing pharmaceutical formulation as claimed in claim 1, wherein the formulation is further packaged in or under an inert atmosphere.

9. The cannabinoid containing pharmaceutical formulation as claimed in claim 8, wherein the inert atmosphere is nitrogen.

10. A method of improving storage stability of a cannabinoid containing pharmaceutical formulation comprising packaging the formulation comprising one or more cannabinoids and one or more pharmaceutically acceptable excipients in packaging to protect it from degradation by light, wherein the packaging comprises a light-excluding foil, and wherein the pharmaceutical formulation comprises an alcoholic solvent.

11. The method as claimed in claim 10, wherein the pharmaceutical formulation comprises one or more of the cannabinoids selected from tetrahydrocannabinol (THC), cannabidiol (CBD), tetrahydrocannabivarin (THCV) and cannabidivarin (CBDV).

12. The method as claimed in claim 11, wherein the pharmaceutical formulation comprises cannabidiol (CBD).

13. The method as claimed in claim 10, wherein the pharmaceutical formulation is packaged so as to prevent ingress of light.

14. The method as claimed in claim 10, wherein the pharmaceutical formulation is packaged to exclude UV light and/or light from the blue region of the spectrum.

15. The method as claimed in claim 10, wherein the cannabinoid is present as an extract or a highly purified pharmaceutical grade substance.

16. The method as claimed in claim 10, wherein the pharmaceutical formulation is packaged in or under an inert atmosphere.

* * * * *

UNITED STATES PATENT AND TRADEMARK OFFICE
CERTIFICATE OF CORRECTION

PATENT NO. : 10,179,683 B2
APPLICATION NO. : 14/685707
DATED : January 15, 2019
INVENTOR(S) : Brian Anthony Whittle Page 1 of 1

It is certified that error appears in the above-identified patent and that said Letters Patent is hereby corrected as shown below:

In the Claims

Claim 15, Column 24, Lines 54-56, should read:
15. The method as claimed in claim 10, wherein the cannabinoid is present as an extract or a highly purified Pharmacopeial grade substance.

Signed and Sealed this
Seventh Day of May, 2019

Andrei Iancu
*Director of the United States Patent and Trademark Office*